United States Patent
Hebb

(10) Patent No.: US 12,247,218 B2
(45) Date of Patent: Mar. 11, 2025

(54) EXPANDABLE CELL POPULATIONS FROM BRAIN BIOPSIES OF LIVING SUBJECTS

(71) Applicant: LONDON HEALTH SCIENCES CENTRE RESEARCH INC., London (CA)

(72) Inventor: Matthew Olding Hebb, London (CA)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 278 days.

(21) Appl. No.: 18/080,811

(22) Filed: Dec. 14, 2022

(65) Prior Publication Data

US 2023/0113275 A1  Apr. 13, 2023

Related U.S. Application Data

(60) Continuation of application No. 16/788,037, filed on Feb. 11, 2020, now abandoned, which is a division of application No. 14/891,393, filed as application No. PCT/CA2014/050461 on May 16, 2014, now abandoned.

(60) Provisional application No. 61/824,125, filed on May 16, 2013.

(51) Int. Cl.
C12N 5/079 (2010.01)
A61K 35/30 (2015.01)
G01N 33/50 (2006.01)

(52) U.S. Cl.
CPC ............ *C12N 5/0618* (2013.01); *A61K 35/30* (2013.01); *G01N 33/5005* (2013.01); *C12N 2510/00* (2013.01); *C12N 2533/32* (2013.01)

(58) Field of Classification Search
None
See application file for complete search history.

(56) References Cited

PUBLICATIONS

Levesque, M., et al., 2009, Open Stem Cell J., vol. 1: pp. 20-29.*
Xu, H. et al., 2013, FASEB J., vol. 27: pp. 4157-4168.*

* cited by examiner

*Primary Examiner* — Michael D Burkhart
(74) *Attorney, Agent, or Firm* — Eduardo Krupnik

(57) ABSTRACT

The present invention relates to a method of producing expandable cultured brain cells. The brain cells are neurotrophic factor (NTF) positive. The expandable cultured brain cells are obtained by culturing a biopsy obtained from the cortical and/or subcortical brain region of a living subject. The biopsies can be obtained during neurosurgical procedures such as deep brain stimulation. The expandable cultured brain cells of the present invention are useful for the treatment of neurological diseases and other medical conditions.

15 Claims, 13 Drawing Sheets

A

B

EXPANDABLE CELL POPULATIONS FROM BRAIN BIOPSIES OF LIVING SUBJECTS

CROSS REFERENCE TO RELATED APPLICATIONS

This application is a continuation of U.S. patent application Ser. No. 16/788,037 filed Feb. 11, 2020, which in turn is a divisional of U.S. patent application Ser. No. 14/891,393 filed Nov. 16, 2015, which in turn is a national stage application under 35 U.S.C. 371 of International Application No. PCT/CA2014/050461, filed May 16, 2014, which in turn claims the benefit under 35 U.S.C. 119(e) of U.S. Provisional Ser. No. 61/824,125, filed May 16, 2013, the contents of each of which are hereby incorporated by reference into the present disclosure.

FIELD OF THE INVENTION

The present invention relates to cell cultures obtained from brain tissues of living subjects, and to methods for their production and use in both research and clinical applications.

BACKGROUND OF THE INVENTION

Parkinson's Disease (PD) is best recognized for degeneration within the dopaminergic mesencephalon but widely affects neurons and non-neuronal cells in the central, peripheral and autonomic nervous systems (1-4). No definitive treatment is available and the current standard of care includes dopamine replacement therapy and deep brain stimulation (DBS) for symptom control.

Various neurotrophic factors (NTFs) have been established as potent cytoprotective agents in the brain and are currently being evaluated for therapeutic potential in PD and other neurological diseases. The four main NTF families are: 1. the glial-derived neurotrophic factor (GDNF) family of ligands (GFL), 2. neurotrophins, 3. neurokines, and 4. the cerebral dopamine neurotrophic factor (CDNF)/mesencephalic astrocyte-derived neurotrophic factor (MANF) family. These proteins regulate vital biological programs in the developing and adult nervous systems and confer broad regenerative and survival effects in experimental PD models (5-11). Clinical application of NTF therapy has been restricted by numerous pharmacological challenges, including poor blood brain barrier permeability, limited tissue diffusion and rapid intraparenchymal metabolism. Various protein modifications have been used to enhance uptake of systemic NTFs into the central nervous system (CNS) and direct delivery into the brain has been achieved using microinfusion pumps and gene transfer methods (10, 12). Despite these technological advances, clinical progress has been slow and there remain concerns regarding appropriate selection of intracerebral delivery sites, adequacy of parenchymal drug levels and immune sensitization to exogenous NTFs.

Embryonic stem cells can be used to regenerate neuronal or glial cells in the brain. However, ethical and logistical considerations have hampered used of ES cells (U.S. Pat. No. 7,923,007).

Transplanted cells with appropriate endogenous or engineered gene expression may serve as biological vehicles or transplant substrate for long-term administration of trophic agents within the PD-affected brain. The efficacy of this approach is largely defined by the durability, disbursement and function of graft cells within target regions. Autologous tissue sources, particularly those of CNS origin, may be well-suited to generate grafts that evade immunological barriers and efficiently integrate into the host environment following transplantation. Unfortunately, the inaccessibility of CNS tissue from living PD patients mandates the use of other cell types that require in vitro transformation or complex genetic reprogramming to confer adaptability and benefit as intracerebral grafts.

DBS is now widely accepted in the management of PD symptomatology (20). The surgical procedure involves minimal cortical exposure to allow stereotactic implantation of intracerebral electrodes. The bony aperture is typically over non-eloquent areas of the frontal lobe and affords a privileged opportunity to sample this brain region with low risk of clinical sequelae.

Brain biopsies in surgical PD patients may provide adequate source tissue to generate autologous and expandable reserves of CNS cells that could be exploited in therapeutic applications.

SUMMARY OF THE INVENTION

The present invention relates to cells and cell cultures obtained from brain tissue, samples or biopsies of living subjects, and to methods for their production and use in both research and clinical applications.

In one embodiment, the present invention provides for a cultured brain tissue-derived cell/cells that is/are positive for at least one neurotrophic factor (NTF).

In one embodiment, the cultured brain tissue-derived brain cell of the present invention is further positive for at least one oligodendrogial protein.

In another embodiment, the cultured brain tissue-derived brain cell of the present invention is further positive for at least one progenitor marker.

In another embodiment, the cultured brain tissue-derived brain cell of the present invention is further positive for at least one mesenchymal protein.

In another embodiment, the cultured brain tissue-derived brain cell of the present invention is further positive for at least one oligodendrogial protein and for at least one progenitor marker.

In another embodiment, the cultured brain tissue-derived brain cell of the present invention is further positive for at least one oligodendrogial protein, for at least one progenitor marker and for at least one mesenchymal protein.

In another embodiment of the cultured brain tissue-derived brain cell of the present invention, the at least one NTF includes members of glial cell line-derived neurotrophic factor (GDNF) family of ligands (GFL), neurotrophin and CDNF/MANF families.

In another embodiment of the cultured brain tissue-derived brain cell of the present invention, the cultured brain tissue-derived brain cell is genetically or physiologically modified to underexpress, express or overexpress a cellular molecule of interest.

In another embodiment of the cultured brain tissue-derived brain cell of the present invention, the cultured brain is non-genetically modified.

In another embodiment of the cultured brain tissue-derived brain cell of the present invention, the cultured brain tissue-derived brain cell is a research grade cell.

In another embodiment of the cultured brain tissue-derived brain cell of the present invention, the cultured brain tissue-derived brain cell is obtained from a living subject.

In one embodiment, the present invention provides for a method of producing expandable brain cells. The method, in one embodiment, includes: (a) harvesting brain cells from a living subject, and (b) expanding the brain cells in a culturing medium thereby producing expanded brain cells.

In one embodiment of the method of producing expandable brain cells, the brain cells are obtained during a neurosurgical procedure of the living subject.

In another embodiment of the method of producing expandable brain cells, the expanded brain cells include cells which are positive for at least one neurotrophic factor (NTF).

In another embodiment of the method of producing expandable brain cells, the expanded brain cells include cells which are further positive for at least one oligodendrogial protein.

In another embodiment of the method of producing expandable brain cells, the NTF includes one or more members of glial cell line-derived neurotrophic factor (GDNF) family of ligands (GFL), neurotrophin and CDNF/MANF families.

In another embodiment of the method of producing expandable brain cells, the expanded brain cells include cells which are further positive at least one oligodendrogial protein and at least one progenitor marker.

In another embodiment of the method of producing expandable brain cells, the expanded brain cells include cells which are further positive for at least one oligodendrogial protein, at least one progenitor marker and at least one mesenchymal protein.

In another embodiment of the method of producing expandable brain cells, the method further comprises genetically or physiologically manipulating the expanded brain cell to underexpress, express or overexpress a molecule of interest.

In another embodiment of the method of producing expandable brain cells, step (b) comprises: (i) culturing the brain cells in a growth medium, and (ii) passaging the cultures of brain cells.

In another embodiment of the method of producing expandable brain cells, the brain cells are produced for in vitro research purposes.

In another embodiment of the method of producing expandable brain cells, the expanded brain cells are produced for the treatment of a neurological disorder or other medical condition in a subject.

In another embodiment of the method of producing expandable brain cells, the expanded brain cells are autologous to the subject.

In one embodiment, the present invention relates to a method of treating a neurological disorder in a subject. The method, in one embodiment, includes: (a) expanding brain cells; and (b) administering an effective amount of the expanded brain cells to the subject, wherein the expanded brain cells promote treatment of the neurological disorder.

The method of treating a neurological disorder in a subject of the present invention, in one embodiment, further includes culturing the brain cells in a culture medium such that the cultured brain cells are non-immunogenic when administered.

In another embodiment of the method of treating a neurological disorder in a subject of the present invention, the culture medium includes brain tissue.

In another embodiment of the method of treating a neurological disorder in a subject of the present invention, the brain cells are obtained during a neurosurgical procedure.

In another embodiment of the method of treating a neurological disorder in a subject of the present invention, the expanded brain cells include cells which are positive for at least one neurotrophic factor (NTF).

In another embodiment of the method of treating a neurological disorder in a subject of the present invention, the expanded brain cells include cells which are further positive for at least one oligodendrogial protein.

In another embodiment of the method of treating a neurological disorder in a subject of the present invention, the NTF includes one or more members of glial cell line-derived neurotrophic factor (GDNF) family of ligands (GFL), neurotrophin and CDNF/MANF families.

In another embodiment of the method of treating a neurological disorder in a subject of the present invention, the expanded brain cells include cells which are further positive at least one oligodendrogial protein and at least one progenitor marker.

In another embodiment of the method of treating a neurological disorder in a subject of the present invention, the expanded brain cells include cells which are further positive for at least one oligodendrogial protein, at least one progenitor marker and at least one mesenchymal protein.

In another embodiment of the method of treating a neurological disorder in a subject of the present invention, the method further includes genetically or physiologically manipulating the expanded brain cell.

In another embodiment of the method of treating a neurological disorder in a subject of the present invention, step (a) includes: (i) harvesting brain cells from a living subject (ii) culturing the brain cells in a growth medium, and (iii) passaging the cultures of brain cells. In one aspect of this embodiment, the subject being treated and the living subject are the same person such that the brain cells are autologous to the subject being treated.

In another embodiment of the method of treating a neurological disorder in a subject of the present invention, the brain cells are autologous to the subject being treated.

In another embodiment of the method of treating a neurological disorder in a subject of the present invention, the brain cells are administered intravenous, intramuscular, intraluminal, intratracheal, intraperitoneal, subcutaneous, intracerebrally, intraventricular or intrathecally.

In one embodiment the present invention is a use of the cultured brain tissue-derived brain cell of the present invention in the treatment of a neurological disorder or other medical condition in a subject.

In one embodiment of the use of the cultured cells in the treatment of a neurological disorder or other medical condition, the cultured brain cells are autologous to the subject.

In yet another embodiment, the present invention provides for use of the cultured brain cells of any the previous embodiments in the treatment of a neurological disorder or other medical condition in a subject. In one embodiment, the cultured brain cells are autologous to the subject.

In another embodiment, the present invention provides for a use of the cultured brain tissue-derived brain cell of any of the previous embodiments for the preparation of a cell composition for use in transplantation therapy of a neurological disease or disorder or other medical condition. In one embodiment, the transplantation is an autologous transplantation.

In another embodiment, the present invention provides for a use of the cell of any of the previous embodiments to optimize culture media for the isolation and cultivation of cells.

In yet another embodiment, the present invention is a method for selecting brain cultured cells for a desired cellular molecule. The method, in one embodiment, includes harvesting brain cells from the brain of a living subject, culturing the harvested brain cells to obtain a culture of expandable brain cells, assaying the expandable cells for the desired cellular molecule, and selecting the expandable brain cells pursuant to said assay.

In one embodiment of the method for selecting brain cultured cells for a desired cellular molecule of the present invention, the desired marker is selected from one or more of: a neurotrophic factor (NTF), an oligodendrogial protein, a progenitor marker, a mesenchymal protein.

In another embodiment, the present invention provides for an isolated brain cell that is positive for at least one neurotrophic factor (NTF).

In one embodiment of the present invention, the isolated brain cell is further positive for at least one oligodendrogial protein.

In another embodiment of the present invention, the isolated brain cell is further positive for at least one progenitor marker.

In another embodiment of the present invention, the isolated brain cell is further positive for at least one mesenchymal protein.

In another embodiment of the present invention, the isolated brain cell is further positive for at least one oligodendrogial protein and for at least one progenitor marker.

In another embodiment of the present invention, the isolated brain cell is further positive for at least one oligodendrogial protein, for at least one progenitor marker and for at least one mesenchymal protein.

In another embodiment of the isolated brain cell of the present invention, the at least one NTF include members of glial cell line-derived neurotrophic factor (GDNF) family of ligands (GFL), neurotrophin and CDNF/MANF families.

In another embodiment of the present invention, the isolated cell is a research grade cell.

In another embodiment of the present invention, the isolated brain cell has been genetically or physiologically modified to underexpress, express or overexpress a cellular molecule of interest.

In another embodiment the present invention relates to a composition comprising the brain tissue-derived cell or cells of the present invention and a carrier.

In one embodiment of the composition of the present invention, the composition further includes brain tissue.

In another embodiment the present invention provides for cultured brain tissue-derived cells that are obtained from a living subject.

In one embodiment of the cultured brain tissue-derived cells, the brain cells are obtained during a neurosurgical procedure.

In another embodiment of the cultured brain tissue-derived cells, the cultured brain tissue-derived cells are genetically or physiologically manipulated.

In another embodiment of the cultured brain tissue-derived cells, the cultured brain tissue-derived cells are positive for one or more of a neurotrophic factor (NTF), an oligodendrogial protein, a progenitor marker, a mesenchymal protein.

Without being bound by any theory of action, the inventor believes the brain cells described herein constitute an expandable source of cell substrate with therapeutic applications in PD and other neurological and medical conditions or diseases.

BRIEF DESCRIPTION OF THE DRAWINGS

The following figures illustrate various aspects and preferred and alternative embodiments of the invention.

DESCRIPTION OF THE INVENTION

Definitions

Figure 1:
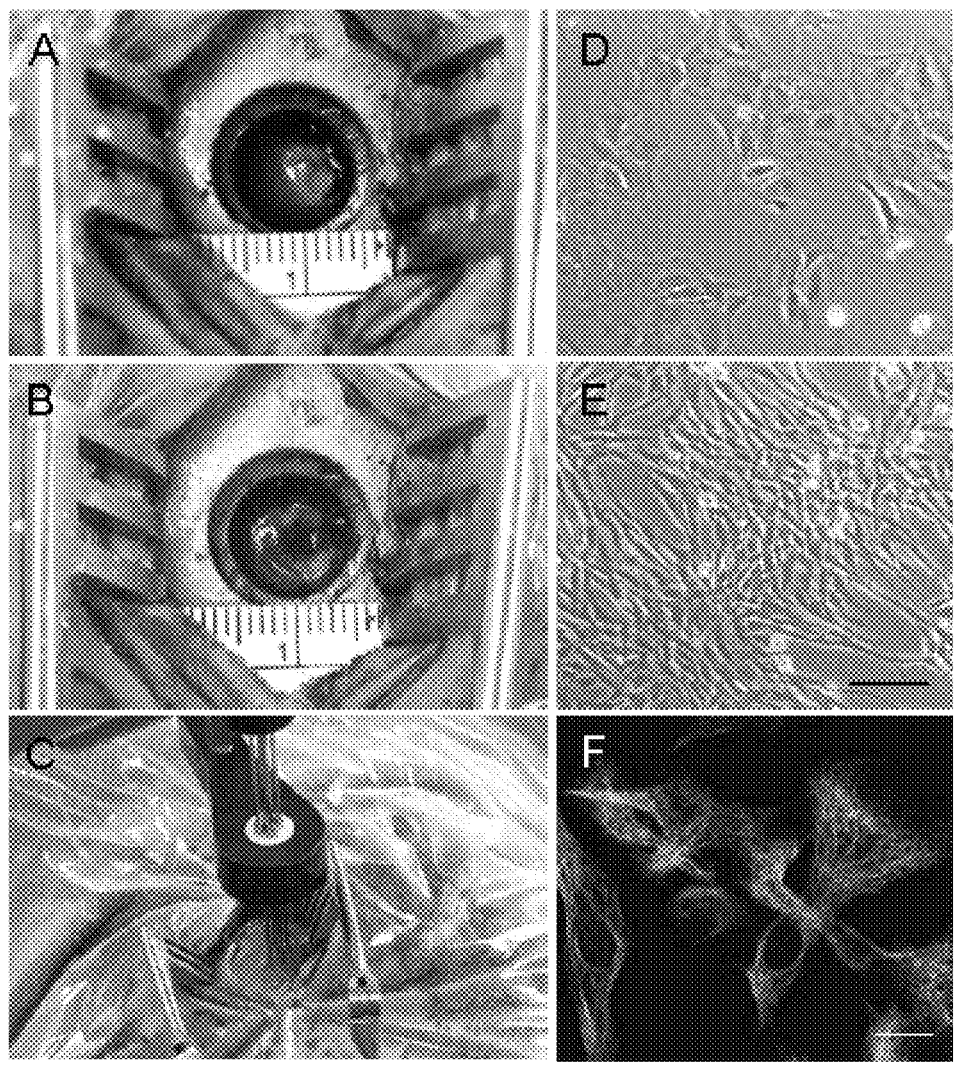
FIG. 1. Brain biopsies in PD patients yield expandable primary cell cultures. A-C) Operative images taken during DBS surgery in a PD patient. A) The cortical exposure was achieved through a 14 mm burr hole and dural opening over the frontal lobe. B) Appearance of the brain following pial incision and brain biopsy. C) The biopsy site was used as the entry portal for the microelectrode array (shown) and subsequent DBS lead. The biopsy tissue yielded cultures with robust proliferative capacity and characteristic morphology. At subconfluence (D), cells were flat with broad polygonal somata and generous cytoplasm while at higher densities (E), the cytoplasm was modest and somata spindle-shaped with fine lamellopodia. F) Cells exhibited robust expression of the progenitor marker, nestin. The scale bar in E) estimates 50 μm for panels D) and E), while that in F) estimates 20 μm.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

"Effective amount" refers to an amount of the composition that is capable of producing a medically desirable result in a treated subject. The methods of the present invention may be performed alone or in combination with other drugs or therapies.

Overexpression of a molecule refers to a molecule that is produced in increased amounts in the cell. This can be achieved, for example, by increasing the copy number of a gene, by placing a gene under a promoter stronger than its own promoter, by mutating a suppressor gene and so forth.

Underexpression of a molecule refers tot a molecule that is not produced or produced in substantially less amounts in a cell.

"Pharmaceutically acceptable" refers to molecular entities and other ingredients of such compositions that are physiologically tolerable and do not typically produce unwanted reactions when administered to a human.

"Research" refers to uses of the cells and methods of the present invention exclusively for laboratory study purposes. That is to say, research-grade cultured cells are not introduced into a human or other animal subject upon cultivation.

"Subject" refers to a human or non-human mammal.

"Treating" refers to administration of a composition, including cell compositions or cells, to a subject who is suffering or is at risk of developing brain tissue damage or a disorder causing such damage, with the purpose to cure, alleviate, relieve, remedy, prevent or ameliorate the damage/disorder.

Overview

The present invention relates to expandable brain cells obtained from brain tissue of a living subject, for example they may be taken at the time of deep brain stimulation (DBS) surgery, to methods of producing the expandable brain cells from brain samples, and to uses of the expandable brain cells. The expandable brain cells may be neurotrophic factor (NTF)-producing cells. The NTF-producing cells of the present invention may be used as transplant substrate or conduit that may provide sustained delivery of endogenous and/or engineered therapeutics, including NTFs, into, for example, a diseased-affected central nervous system. The NTF-cells of the present invention may be amenable for in vivo cell tracking and gene-based magnetic resonance imaging contrast enhancement methods. The expanded brain cells of the present invention may be non-genetically modified or genetically modified. The expanded brain cells of the present invention may be genetically or physiologically modified to underexpresses (i.e. inhibit, attenuate, ameliorate and so forth), express, or overexpress a desired cellular molecule, including proteins, nucleic acids, lipids, sugars and so forth. As such, the NTF-cells of the present invention may be used for both human and non-human animal research and clinical applications. Clinical applications may include both human and veterinary clinical applications.

Brain Cell Cultures

The present invention, in one embodiment, relates to isolating and culturing brain cells derived from biopsies of living subjects, which may be used in the treatment of central nervous system-related disorders.

Brain biopsies from living individuals may be obtained, for example, from patients undergoing a procedure, such as, for example, during DBS.

For sustained and effective cell therapy, an ideal graft may include autologous drug (e.g., dopamine, NTF)-producing cells of CNS origin that are well-suited to reintegrate into the host environment following transplantation. The Applicants discovered that brain cells cultured from biopsies obtained from cortical and/or subcortical brain sites result in a substantially homogeneous population of cells that express at least one neurotrophic factor (NTF). The demonstration of NTFs expression in these preparations is inventive and includes members of the glial derived neurotrophic factor (GDNF) family of ligands (GFL), neurotrophin (i.e., BDNF), and cerebral dopamine neurotrophic factor (CDNF)/mesencephalic astrocyte-derived neurotrophic factor (MANF) families, each of which having extensively demonstrated to have protective and/or regenerative benefits in preclinical Parkinson's Disease (PD) models (10). The Applicant further demonstrated that the cells cultured from the brain biopsies may be positive for NTF(s) and oligodendrocyte proteins. The brain cells cultured of the present invention may also concurrently express NTF, at least one oligodendrocyte protein, a progenitor cell marker and at least one mesenchymal protein.

To prepare the brain cell cultures, one can use the method described in Example 1 below.

To confirm that the cultured cells are NTF positive, or that they concurrently express at least one NTF, at least one oligodendrocyte protein, at least one progenitor cell marker and at least one mesenchymal protein, the cells may be tested or assayed by standard analyses, such as immunochemical analysis as provided in the Examples herein below.

The cultured brain cells may be propagated in growth medium for 10 or more passages.

The cultured cells may be stored by standard methods known in the art (see Example 1) or they may be administered, intracerebrally, intraventricularly or intrathecally or by any other effective delivery route, to a subject in need. The cells may be administered to the subject at one or more than one site. If the subject undergone DBS, the cells, in one embodiment, may be administered at the sites that serve as electrode insertion points. Administration of the cells of the present invention may be autologous or allogenic to the subject receiving the cells. In the case of autologous administration, the cultured cells of the present invention may be administered to desired brain regions through the cerebral defect at the collection site, or through different brain insertion sites. In the case of allogenic administration, the cultured cells of the present invention may be administered to desired brain regions through a cerebral defect, or through different brain insertion sites.

Compositions

The cultured brain cells of the present invention may be used to prepare compositions such as pharmaceutical or research compositions.

In one embodiment, the present invention provides for a composition that may include expanded brain cells of the present invention, which may be NTF-positive brain cells. In another embodiment the composition may include the expanded brain cells of the present invention and a brain tissue.

Pharmaceutical compositions may be prepared by mixing a therapeutically effective amount of the cells of the present invention, and, optionally other active substance, with a pharmaceutically acceptable carrier. The carrier may have different forms, depending on the route of administration.

The pharmaceutical compositions may be prepared by using conventional pharmaceutical excipients and methods of preparation. All excipients may be mixed with disintegrating agents, solvents, granulating agents, moisturizers, and binders. An effective amount of the brain cells may be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions of the present invention refers to a diluent, excipient, or vehicle with which a compound is administered. Such pharmaceutical carriers may be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The brain cells of the present invention may be administered to individuals through infusion or injection (for example, intravenous, intracerebral, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells may be used. In the former case, HLA-matching may be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

Methods and Uses

The present invention, in one embodiment, provides for a method of treating neurological disorders or other medical conditions and for NTF positive cells for use in the treatment of neurological disorders or other medical conditions. The method, in one embodiment, includes administering to a subject in need, such as a subject suffering from a neurological disorder or other medical condition or at risk of developing a neurological disorder or other medical condition, an effective amount of the expanded brain cells of the present invention.

Neurological disorder may include neurodegenerative diseases including PD, Alzheimer's disease, Spinocerebellar disease, or Huntington Disease. The neurological disorder may also include brain tissue damage caused by a cerebral ischemia, such as in stroke. The therapeutic effects of the treatment may be assessed according to standard techniques known in the art, including imaging techniques (MRI, CT, Doppler ultrasound, and so forth). The subject may be assessed before and after the treatment.

In one embodiment, the above-described cells and methods may be used to facilitate the efficient establishment of ex-vivo expanded populations of cells derived from brain samples, which may be taken at the time of deep brain stimulation (DBS) surgery or other cranial neurosurgical procedure, suitable for transplantation into the central nervous system. Specifically, the ex-vivo expanded brain cells may be used to treat diseases of the central nervous system or other medical condition. The methods of the invention may also be used for applications in cellular gene therapy of transplanted, repopulated organs.

The specific examples below are to be construed as merely illustrative, and not limitative of the remainder of the disclosure in any way whatsoever. Without further elaboration, it is believed that one skilled in the art can, based on the description presented herein, utilize the present invention to the full extent. All publications cited and the priority document are incorporated herein by reference. Any mechanism proposed below does not in any way restrict the scope of the claimed invention.

Example 1—Materials and Methods

Patient Selection and Deep Brain Stimulation (DBS) Surgery

This study has been approved by the Research Ethics Board at the University of Western Ontario. Subject eligibility required an unequivocal diagnosis of Parkinson's Disease (PD) and neuropsychological and medical fitness for DBS surgery. Informed consent was obtained from each patient for both DBS surgery and study participation.

Patients suitable for surgery but with anatomy deemed unfavorable for biopsy (e.g., marked cerebral atrophy, prominent vasculature) on preoperative imaging or at the time of operation were excluded. The procedures were performed with the subthalamic nucleus as the DBS target, defined by standardized coordinates and corrected to the patient's anatomy. Burr holes (14 mm) were created in the skull over non-eloquent areas of the frontal lobes to accommodate placement of microelectrodes and DBS leads. A 5-channel microelectrode array was used for electrophysiological mapping and stimulation testing with the patient awake. With satisfactory target localization, the microelectrodes were removed and a DBS lead (Activa 3389, Medtronic) implanted. A pulse generator (Kinetra® or Activa PC®, Medtronic) was then housed in the subcutaneous tissue of the upper chest and connected to the distal end of the DBS leads with subcutaneous extension wires. Computed tomography and/or magnetic resonance imaging were obtained within 72 hours following surgery to evaluate lead position and assess for cerebral infarction or hemorrhage.

Brain Biopsies and Primary Cell Cultures

The DBS protocol was modified with a brain biopsy performed through the burrhole exposure, prior to microelectrode insertion. The dura was widely opened and the pia disrupted sharply. A microdissector was used to remove about 0.5 cc volume of tissue from directly beneath the cortical surface, after which the surgical procedure was carried out in standard fashion. Specimens from bilateral sites were combined as a single tissue source for each patient. The brain samples were immediately placed in phosphate-buffered saline (PBS) with 0.5% fetal bovine serum (FBS) for transport from the operating room to the laboratory, followed by a 20-minute digestion with 0.25% trypsin (Life Technologies Inc., Burlington, ON, Canada) plus DNase I (75 µg; Roche, Laval, P Q, Canada) in a 5 ml volume of PBS at 37° C. After filtering through a 100 µm cell strainer (BD Biosciences, Mississauga, ON, Canada), the brain tissue was centrifuged at 1200 rpm for 10 minutes, then re-suspended in Dulbecco's modified Eagle's medium (DMEM) supplemented with 10% FBS, 1% non-essential amino acids and 1% penicillin/streptomycin before plating to a 35 mm dish for 2 hours to allow blood cells to separate (Life Technologies Inc., Burlington, ON, Canada). The upper cell suspension was then transferred to 2 wells of a 24-well plate, freshly pre-coated with 10 µg/ml poly-L-lysine (Trevigen Inc., Gaithersburg, MD, USA) and incubated at 37° C. in a humidified 5% CO2 atmosphere. Cultures were passaged at approximately 80% confluence and split 1:2 using 0.25% trypsin with 0.53 mM ethylenediaminetetraacetic acid (Wisent Bioproducts, St. Bruno, PQ, Canada). The medium was changed twice per week. At various passages, cells were resuspended in a freezing solution of DMEM with 20% FBS and 10% dimethyl sulfoxide. Aliquots ($5\times10^6$ cells/ml) were placed in cryogenic storage vials and frozen using a CoolCell® freezing container (BioCision LLC, Mill Valley, CA, USA) prior to transfer to a −80° C. freezer or liquid nitrogen. Phenotype analysis was performed during passages 4 through 6 to select for proliferating and progeny cells, when the cultures were characteristically homogeneous in morphology and exhibited rapid growth.

Western Blot Analysis

Cells from the primary cell cultures were collected in lysis buffer (50 mM Tris HCl, 150 mM NaCl, 1% Nonidet P40, pH 7.4) supplemented with SIGMAFAST™ Protease Inhibitor cocktail (1:10; Sigma Aldrich, St Louis, MO, USA), incubated on ice for 15 minutes then sonicated. The cell lysates were centrifuged at 13,000 g for 15 minutes and the protein supernatant collected. Protein similarly isolated from a frozen sample (170 mg) of non-pathological brain was used as a positive control for neural markers not expressed in the PD cells. Protein concentrations were determined using a DC Protein Assay kit (Bio-Rad Laboratories Ltd, Mississauga, ON, Canada) and all fractions were frozen at −80° C. until use. Twenty micrograms of each protein extract were separated on a 12% sodium dodecyl sulphate polyacrylamide gel and transferred electrophoretically to Immun-Blot® PVDF membranes (Bio-Rad Laboratories Ltd., Mississauga, ON, Canada). The membranes were blocked in 5% powdered non-fat milk in Tris-buffered saline with 0.1% Tween-20 at room temperature for 1 hour, then incubated overnight at 4° C. in the same solution containing primary antibodies (Table 1). Membranes were washed in Tris-buffered saline with 0.1% Tween-20 then incubated with a horseradish peroxidase-conjugated, goat anti-rabbit or goat anti-mouse secondary antibody (1:3000; Bio-Rad Laboratories Ltd, Mississauga, ON, Canada) for 1 hour at room temperature. Peroxidase activity was visualized using an enhanced chemiluminescence and detection system imager (GE Healthcare Biosciences, Piscataway, NJ, USA).

Membranes were stripped using a buffer containing 10% sodium dodecyl sulfate solution (20 ml), Tris HCl (12.5 ml, pH 6.8, 0.5M), ultrapure water (67.5 ml) and β-mercaptoethanol (0.8 ml) at 50° C. for up to 45 minutes, followed by washing in ultrapure water (2 hours) then Tris-buffered saline with 0.1% Tween-20 (5 minutes).

The membranes were blocked and re-probed for β-actin as a loading control.

Immunocytochemistry and Microscopy

Cells were plated for 3 days on 12 mm round cover glasses (VWR International, Mississauga, ON, Canada) then washed in PBS, fixed for 20 minutes in 4% paraformaldehyde and permeabilized for 10 minutes in PBS containing 0.25% Triton X-100. Non-specific protein binding was blocked with 1% bovine serum albumin (EMD Millipore Corp., Billerica, MA, USA) prior to incubation with primary antibodies overnight at 4° C. (Table 1). Cells were then washed in PBS and incubated with Alexa Fluor® 488 goat anti-mouse IgG and/or Alexa Fluor® 546 goat anti-rabbit IgG secondary antibodies (1:100) for 1 hour at room temperature and counter-stained with 4'-6-diamidino-2-phenylindole (DAPI) for nuclear visualization (Life Technologies Inc., Burlington, ON, Canada). Control cover glasses were processed in parallel without primary antibody. Cells were imaged using a Zeiss LSM-510 META laser-scanning microscope with a Zeiss 63× NA 1.4 oil immersion lens, appropriate filters and AIM software (Carl Zeiss GmbH, Jena, Germany). Brightfield images of live cells were obtained using a Motic AE31 inverted microscope fitted with an Infinity1-3 scientific complementary metal-oxide semiconductor camera (Lumenera Corp., Ottawa, ON, Canada).

Reverse Transcription-Polymerase Chain Reaction (RT-PCR) and Nucleotide Sequencing Total RNA was isolated from $5\times10^5$ cells using PureLink® RNA Mini Kit (Life Technologies Inc., Burlington, ON, Canada). For each sample, cDNA was generated from 1 μg RNA using SuperScript® II Reverse Transcriptase (Life Technologies Inc., Burlington, ON, Canada). A 1 μl aliquot of the cDNA solution was then added to a PCR mixture containing 0.2 mM dNTP, 0.5 μM oligonucleotide primer and 1 U Taq DNA polymerase, to a final volume of 20 μl. cDNA was amplified using custom primers for human GDNF (forward cggacgggactttaagatga (SEQ ID NO:1); reverse ggaagcactgccatttgttt (SEQ ID NO:2)), BDNF (forward ttggctgacactttcgaacacatga (SEQ ID NO:3); reverse tgccgccgttacccactcac (SEQ ID NO:4)), CDNF (forward gcatatgcctgcaatgaaga (SEQ ID NO:5); reverse agctctgttttggggtgtgt (SEQ ID NO:6)) or glyceraldehyde 3-phosphate dehydrogenase (GAPDH; forward ggtgaagcaggcgtcggagg (SEQ ID NO:7); reverse ggctggtggtccaggggtct (SEQ ID NO:8)) mRNA (Life Technologies Inc., Burlington, ON, Canada). Standard agarose gel electrophoresis was performed and visualized with ethidium bromide (0.5 μg/ml) using a digital imaging system (Alpha Innotech Corp., San Leandro, CA, USA). Each sample was evaluated in duplicate and considered to be positive if a specific amplification product was detected in both assays. Nuclease-free water was used as a negative control during the process. RT-PCR products were purified using a PureLink™ Gel Extraction Kit (Life Technologies Inc., Burlington, ON, Canada) according to the manufactur-

TABLE 1

| Antibody | Catalogue number | Host Species | Dilution (ICC) | Dilution (Western blot) | Vendor |
| --- | --- | --- | --- | --- | --- |
| Nestin | ab22035 | Mouse (monoclonal) | 1:100 | 1:1000 | Abcam |
| CD133 | MAB4399 | Mouse (monoclonal) | 1:100 | 1:1000 | Millipore |
| GLAST | ab41751 | Rabbit (polyclonal) | 1:200 | 1:1000 | Abcam |
| p75$^{NTR}$ | ab38335 | Rabbit (polyclonal) | 1:200 | 1:1000 | Abcam |
| SOX10 | ab107532 | Rabbit (polyclonal) | 1:200 | 1:1000 | Abcam |
| βIII Tubulin | G7121 | Mouse (monoclonal) | 1:100 | 1:1000 | Promega |
| GFAP | ab10062 | Mouse (monoclonal) | 1:200 | 1:1000 | Abcam |
| Iba1 | ab15690 | Mouse (monoclonal) | 1:100 | 1:1000 | Abcam |
| GalC | MAB342 | Mouse (monoclonal) | 1:100 | 1:500 | Millipore |
| Olig1 | MAB5540 | Mouse (monoclonal) | 1:100 | 1:500 | Millipore |
| Collagen I | ab34710 | Rabbit (polyclonal) | 1:200 | 1:1000 | Abcam |
| Collagen III | ab7778 | Rabbit (polyclonal) | 1:200 | 1:1000 | Abcam |
| Fibronectin | F3648 | Rabbit (polyclonal) | 1:200 | 1:1000 | Sigma-Aldrich |
| β-actin | ab49900 | Rabbit (polyclonal) | N/A | 1:20000 | Abcam |
| GDNF | ab18956 | Rabbit (polyclonal) | 1:100 | 1:1000 | Abcam |
| BDNF | ab108383 | Rabbit (polyclonal) | 1:100 | 1:1000 | Abcam |
| CDNF | ab122871 | Rabbit (polyclonal) | 1:100 | 1:1000 | Abcam |
| Anti-human cytoplasm | AB-121-U-050 | Mouse (monoclonal) | 1:40 | | Stemcells Inc | er's protocol. Nucleotide sequencing was performed at the London Regional Genomics Centre (London, ON, Canada; http://www.lrgc.ca/) using an Applied Biosystems 3730 DNA Analyzer (Life Technologies Inc., Burlington, ON, Canada). The sequence specificity of isolated RT-PCR products were confirmed using the Basic Local Alignment Search Tool (http://blast.ncbi.nlm.nih.gov/Blast.cgi).

Example 2—Expandable Cell Cultures Generated from Brain Biopsies in Living PD Patients Specimens were collected from the frontal lobes of 19 PD patients, aged 53 to 73 years. The extent of pial disruption was defined by local gyral and vascular anatomy, and these sites served as microelectrode insertion points following specimen collection (FIGS. 1A-C). The combined volume of bilateral frontal lobe tissue in each patient varied between about 0.5-1.0 cc. One patient had a unilateral DBS procedure and another had favorable anatomy only on a single side. There were no clinical or radiological complications during postoperative periods that ranged between 1-26 months.

The initial tissue preparations yielded morphologically heterogeneous cultures with robust proliferation that commenced between 1-2 weeks after plating. Cells divided rapidly for 6-10 passages after which proliferation slowed. By the fourth passage, cultures appeared homogeneous and subconfluent cells had a characteristic appearance with flat, polygonal somata and broad processes. At higher densities, cell cytoplasm was modest and somata spindle-shaped with fine lamellopodia (FIGS. 1D, E). Cell aliquots frozen for as long as one year were resurrected and viable upon re-plating, with growth kinetics comparable to non-frozen cells.

Example 3—Mixed Lineage Markers are Expressed in Expanded PD Brain Cultures

Figure 2:
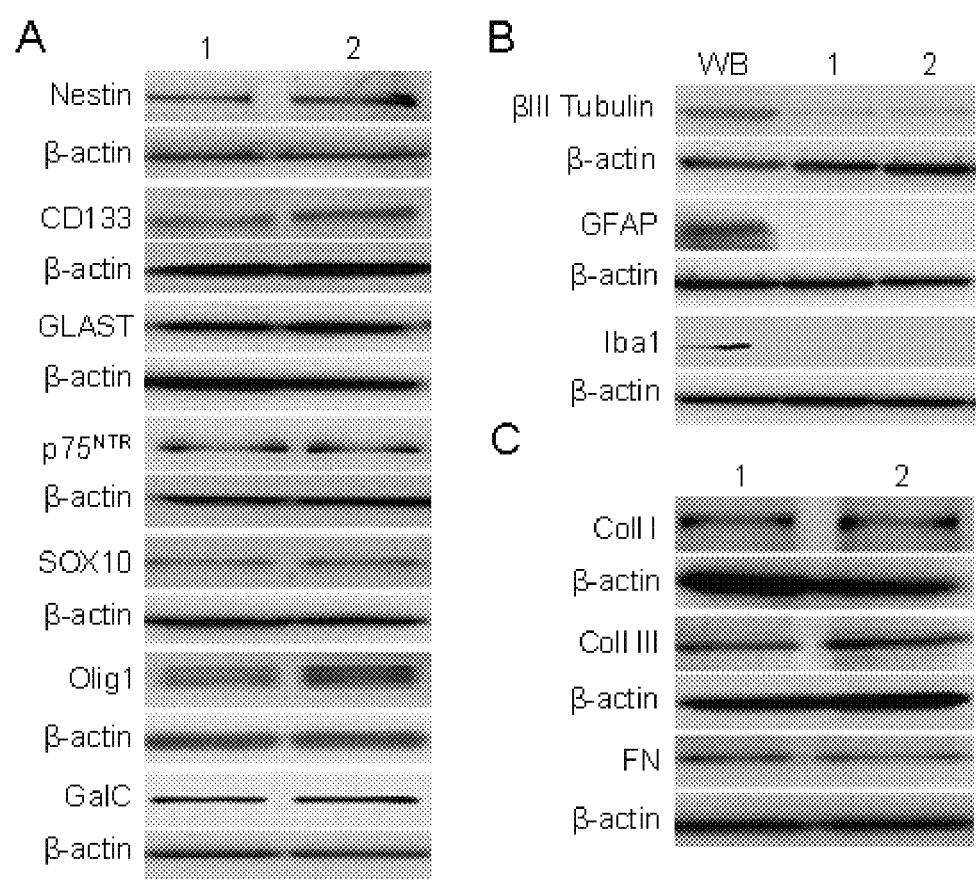
FIG. 2. Lineage markers in primary PD brain cultures. Representative Western blot analysis using cell lysate from the brain cultures of two different PD patients (lanes 1 and 2). A) Specific bands of predicted size were identified for the stem/progenitor cell markers nestin (176 kDa) and CD133 (97 kDa), as well as the respective glial and neural crest proteins, GLAST (56 kDa) and p75NTR (70 kDa). SOX10 (50 kDa) plays a role in neural crest development and oligodendrocyte ontogeny and was reliably identified, in addition to the oligodendrocyte markers, Olig 1 (27 kDa doublet) and GalC (75 kDa). B) There was scant expression of the neuronal marker βIII tubulin (55 kDa) and no detection of the respective astrocyte and microglial markers, GFAP (45 kDa) and Iba1 (20 kDa). Protein isolated from normal whole brain (WB) samples served as a positive control in these analyses. C) The mesenchymal proteins collagen I (138 kDa), collagen III (138 kDa) and fibronectin (220 kDa) were consistently identified. β-actin (42 kDa) served as a loading control and is shown beneath each corresponding lineage marker. Coll I, collagen I; Coll III, collagen III; FN, fibronectin; GalC, galactocerebroside.
Figure 3:
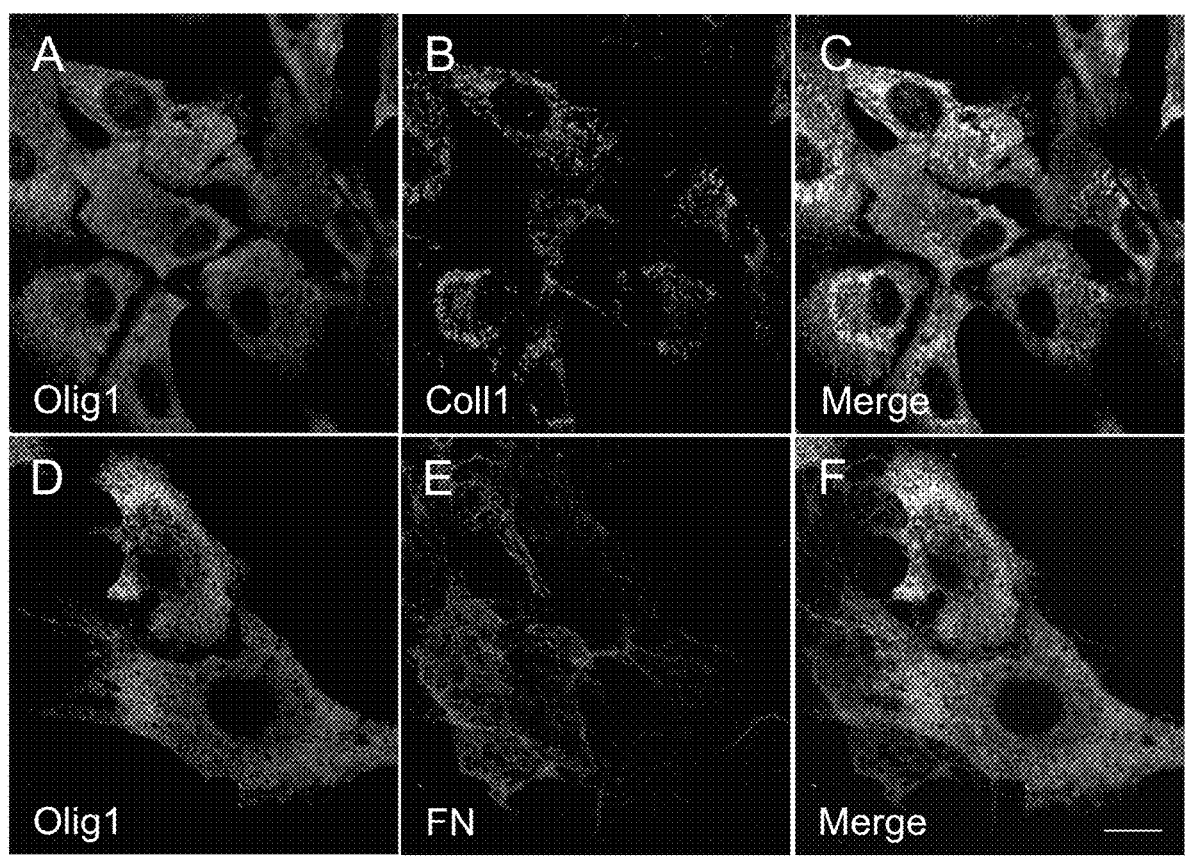
FIG. 3. The oligodendrocyte marker, Olig1, is co-expressed with mesenchymal proteins in expanded cell cultures from PD brain biopsies. Confocal micrographs show two representative cell fields double immunolabeled for Olig1 (green stain) and collagen I (red stain, panels A-C) or fibronectin (red stain, panels D-F). Cells in merge panels C and F show red and green stain, confirming the co-expression of Olig1 with the mesenchymal proteins. The expression of collagen III was similar to that of collagen I (data not shown). The scale bar represents 20 μm. Coll I, collagen I; FN, fibronectin.
Figure 4:
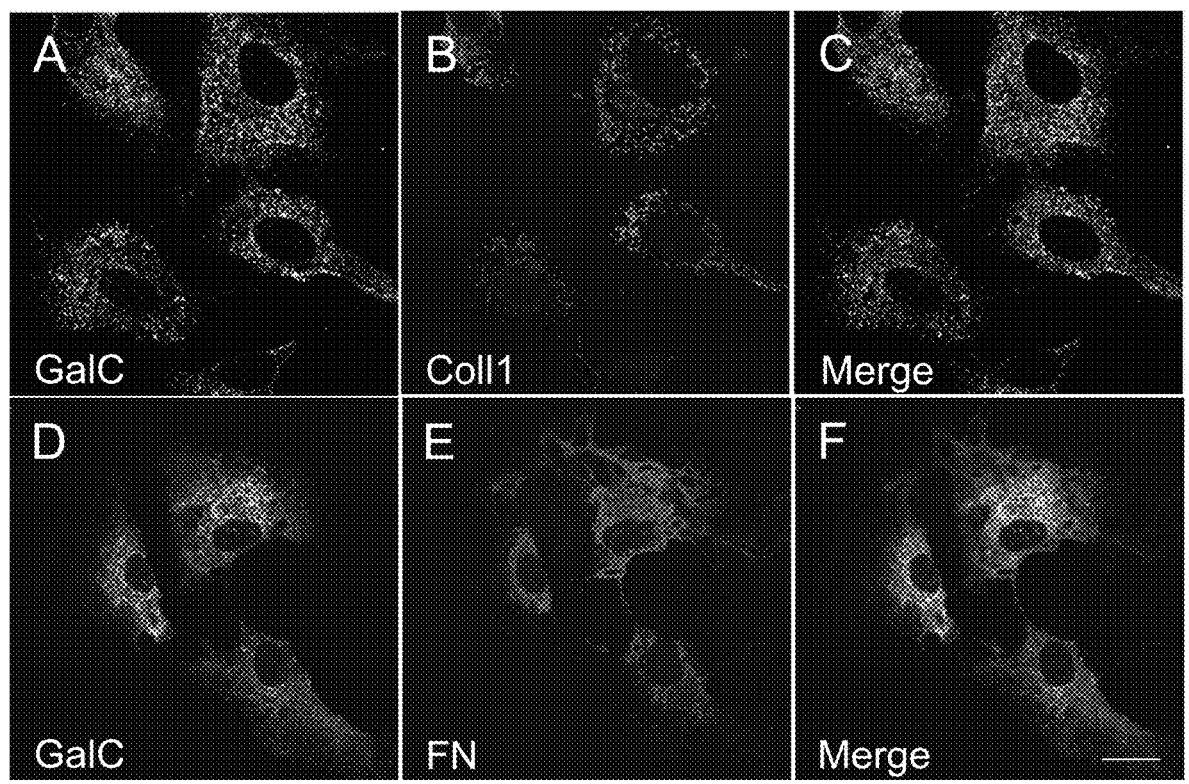
FIG. 4. Confocal micrographs illustrating that the oligodendrocyte marker, galactocerebroside, is co-expressed with mesenchymal proteins in expanded cell cultures from Parkinson's Disease (PD) brain biopsies. The confocal micrographs show two representative cell fields double immunolabeled for GalC (green stain) and collagen I (red stain, panels A-C) or fibronectin (green stain, panels D-F). Cells in merge panels C and F show red and green stain, confirming the co-expression of galactocerebroside with the mesenchymal proteins. The expression of collagen III was similar to that of collagen I (data not shown). The scale bar represents 20 μm. Coll I, collagen I; FN, fibronectin; GalC, galactocerebroside.

Cell phenotype was assessed by categorically defining the expression of progenitor, differentiated neural (i.e., neuronal, astrocytic, microglial, oligodendroglial) and mesenchymal proteins. The cells exhibited robust expression of the progenitor/stem cell marker, nestin, with less intense levels of CD133 evident on Western blot analysis and immunocytochemistry (FIGS. 1F and 2A). The glutamate aspartate transporter (GLAST), p75 neurotrophin receptor (p75NTR) and neural crest/glial-associated transcription factor, SOX10, were reliably observed. The oligodendrocyte lineage gene, Olig1, and the myelin-specific sphingolipid, galactocerebroside (GalC), also an oligodendocyte marker, were labeled in all samples analyzed (FIG. 2A). There were scant levels of the neuronal marker, βIII tubulin, and no detectable expression of the astrocyte or microglial proteins, glial fibrillary acidic protein (GFAP) and ionized calcium binding adaptor molecule 1 (Iba1), respectively (FIG. 2B). Both oligodendroglial markers, Olig1 and GalC, were co-expressed with nestin (data not shown) and the mesenchymal proteins, collagen I, collagen III and fibronectin (FIGS. 2C, 3 and 4).

Example 4—PD Brain Cultures Exhibit a Broad Profile of NTF Expression

Figure 5:
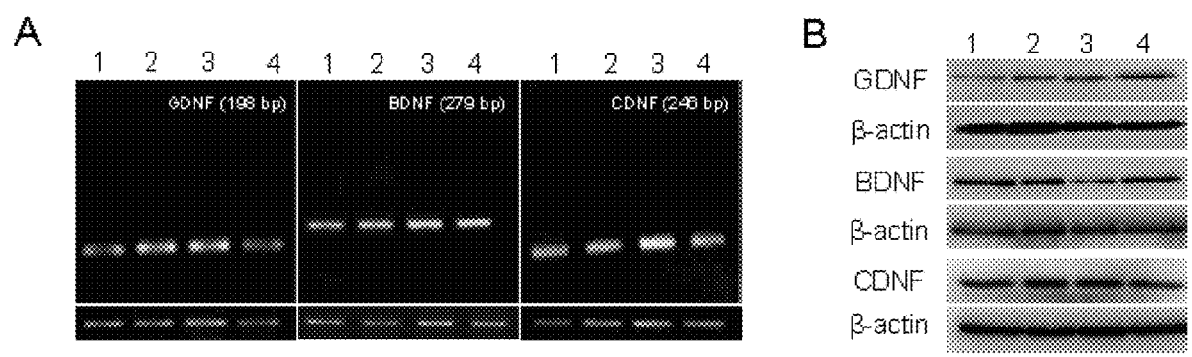
FIG. 5. PD brain cultures exhibit a broad profile of NTF expression. In panels A and B lanes 1-4 represent samples from individual patients. A) RT-PCR analysis demonstrated a single transcript of predicted size, with sequence specificity confirmed for each NTF. GAPDH (247 bp) served as an internal control and is shown in the corresponding lower panels. B) Western blot analysis demonstrated specific protein bands of appropriate molecular weight for GDNF (24 kDa), BDNF (28 kDa) and CDNF (18 kDa). The corresponding β-actin blot (42 kDa) is shown below that of each NTF.

A single cDNA transcript of predicted size was identified for each neurotrophic factor (NTF) in all patient samples evaluated (FIG. 5A). The sequence of the amplified glial-derived neurotrophic factor (GDNF) product was identical to those reported for human GDNF transcript variants published as Genbank accession numbers NM_199231.2, NM_001190469.1, NM_001190468.1 and NM_000514.3. The amplified BDNF product was identical to the known sequences of human BDNF transcript variants published as Genbank accession numbers NM_170735.5, NM_001143816.1, NM_170734.3, NM_001143813.1, NM_001709.4, NM_001143814.1, NM_001143812.1, NM_001143809.1, NM_001143808.1, NM_001143810.1, NM_001143811.1, NM_170733.3, NM_001143807.1, NM_001143806.1, NM_001143805.1, NM_170732.4 and NM_170731.4. The amplified cerebral dopamine neurotrophic factor (CDNF) product was identical to the known sequence of human CDNF transcript variant published as Genbank accession number NM_001029954.2.

Figure 6:
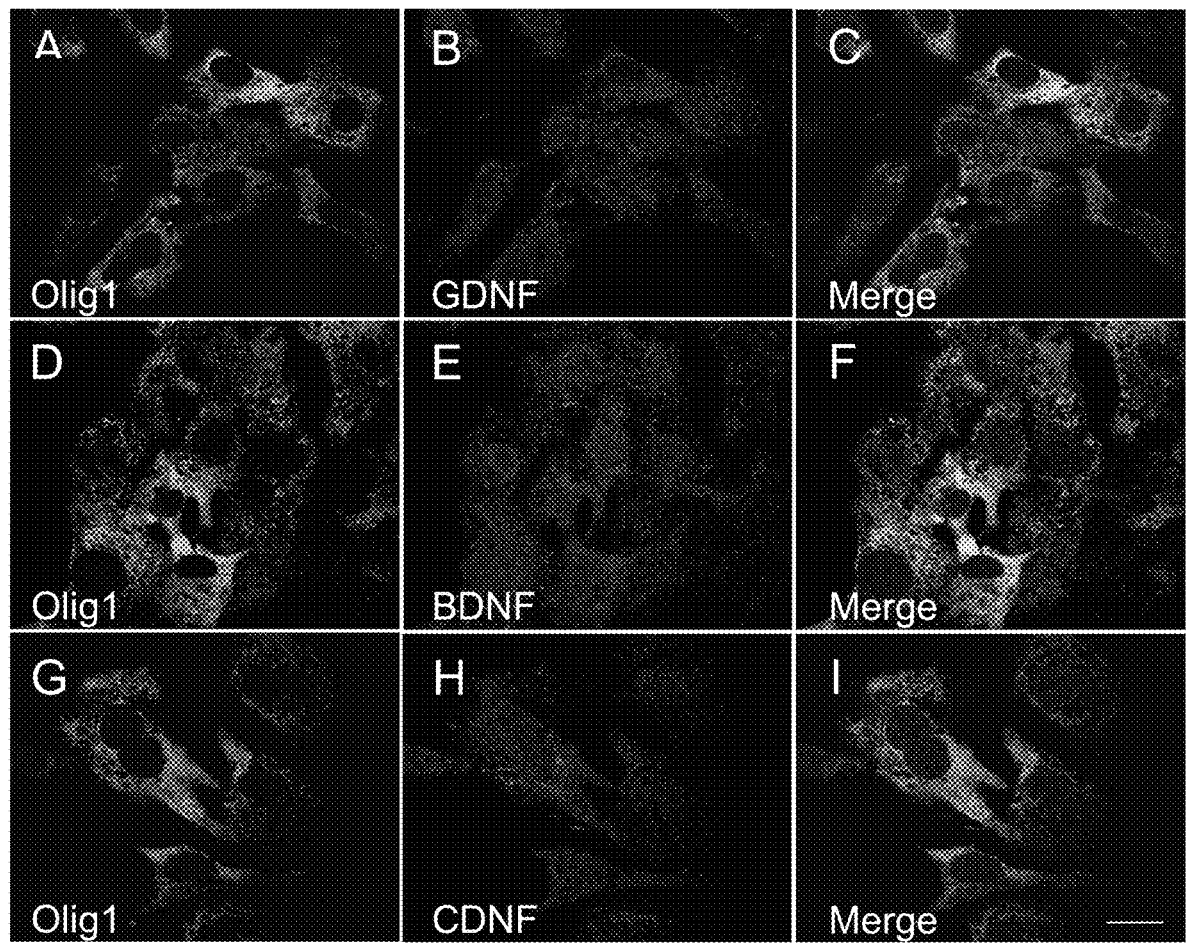
FIG. 6. Confocal micrographs illustrating that cells from expanded PD brain cultures co-express the oligodendrocyte marker, Olig1, and multiple cytoprotective NTFs. Confocal micrographs show three representative cell fields double immunolabeled for Olig1 (green stain) and GDNF (stains red, panels A-C), BDNF (red stain, panels D-F) or CDNF (red stain, panels G-I). Each NTF was reliably expressed and co-localized with Olig1. Cells in merge panels C, F and I show red and green stain confirming the co-expression. The scale bar represents 20 μm. BDNF, brain derived neurotrophic factor; CDNF, cerebral dopamine neurotrophic factor; GDNF, glial-derived neurotrophic factor.
Figure 7:
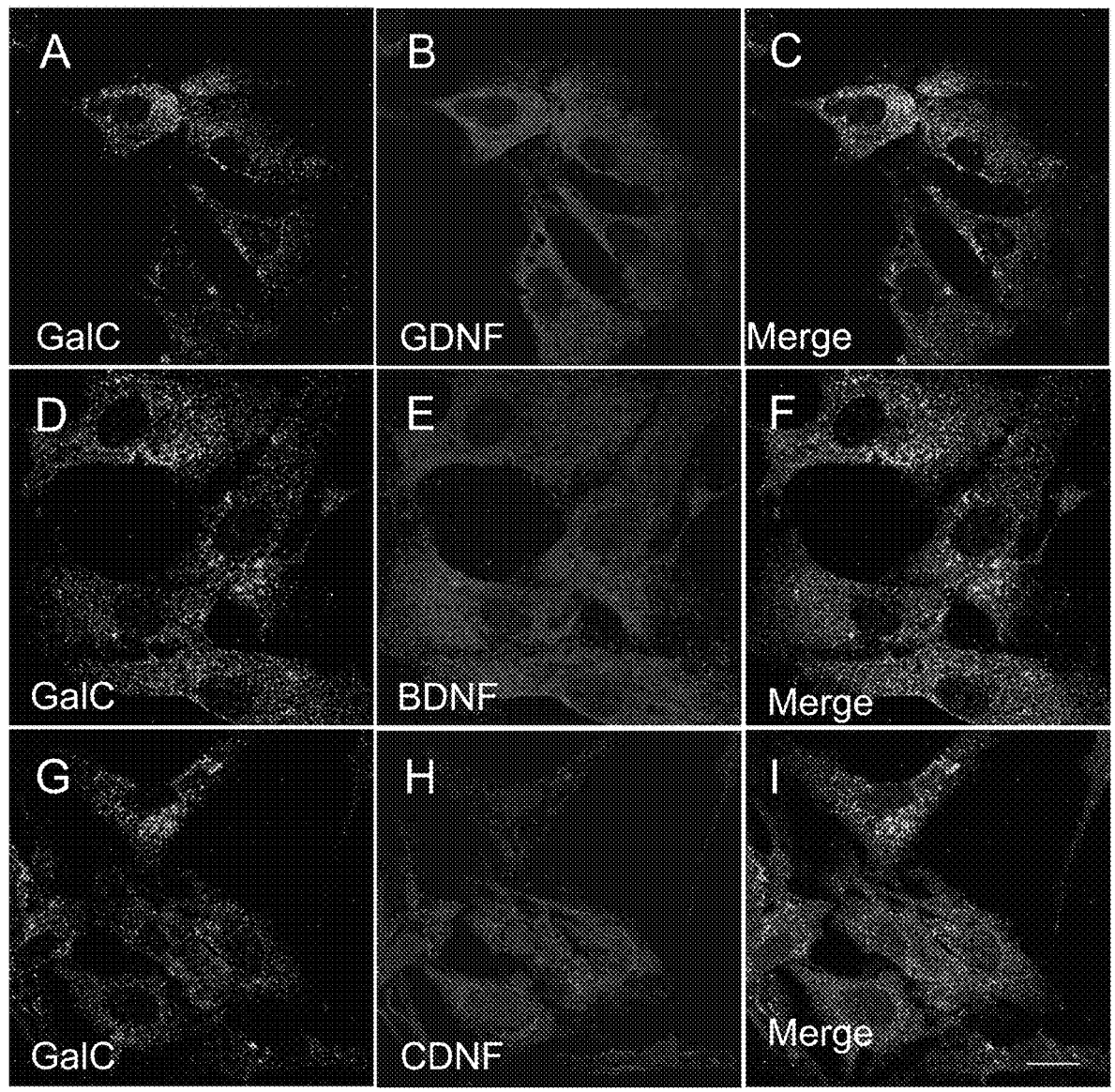
FIG. 7. Cells from expanded PD brain cultures co-express the oligodendrocyte marker, galactocerebroside, and multiple cytoprotective NTFs. Confocal micrographs show three representative cell fields double immunolabeled for galactocerebroside (green stain) and GDNF (red stain, panels A-C), BDNF (red stain, panels D-F) or CDNF (red stain, panels G-I). Each NTF was reliably expressed and co-localized with GalC. Cells in merge panels C, F and I show red and green stain confirming the co-expression. The scale bar represents 20 μm. BDNF, brain derived neurotrophic factor; CDNF, cerebral dopamine neurotrophic factor; GalC, galactocerebroside; GDNF, glial-derived neurotrophic factor.

NTF protein expression was assessed using Western blot analysis and immunocytochemistry, with bands of predicted size and cytoplasmic expression of GDNF, BDNF and CDNF detected in all samples evaluated (FIG. 5B). Double-labeling studies confirmed co-localization of each NTF with the oligodendroglial markers, Olig1 (FIG. 6) and GalC (FIG. 7). Control cells prepared without primary antibody showed no signal for either secondary fluorochrome (data not shown).

Example 5—Nestin

Figure 8:
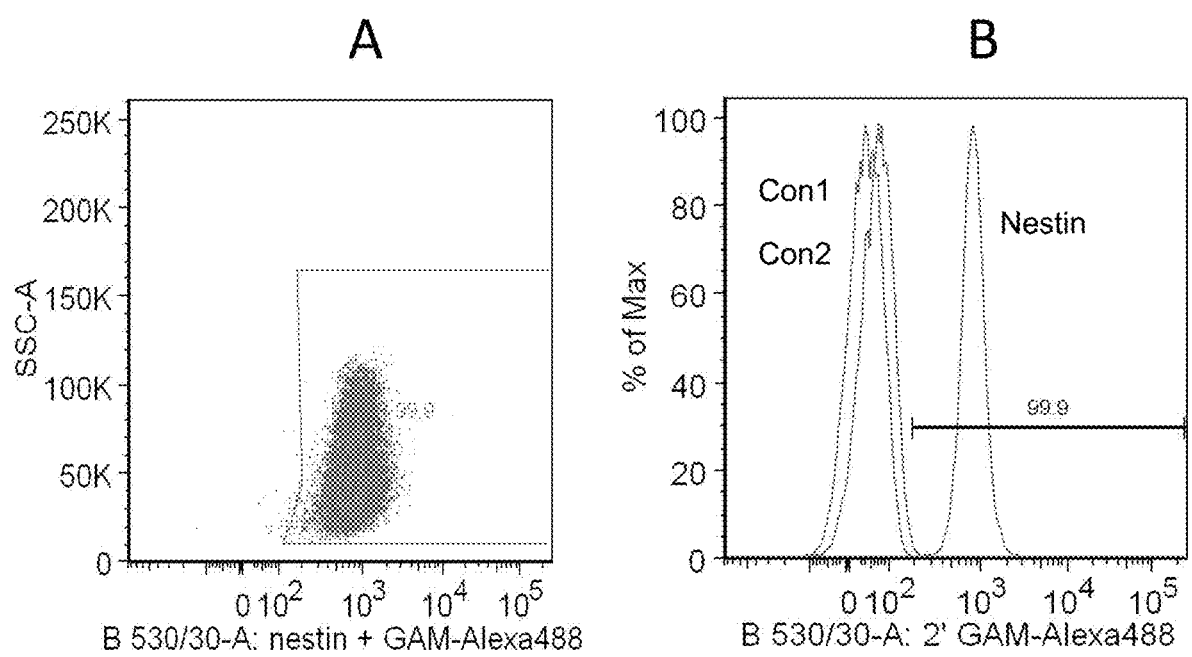
FIG. 8. Fluorescence assisted cell sorting (FACS) for nestin-expressing cells in human PD brain cultures. A: dot plot and gating for the nestin analysis. B: graph illustrating the results of the nestin-labeled and control cell sorts.

Fluorescence assisted cell sorting (FACS) for nestin-expressing cells in human PD brain cultures. The data were acquired using a LSRII flow cytometer with FACSDiva software (BD). FACS data were analyzed with FlowJo (v9.5.2). Approximately 50,000 cells at passage 6 or 7 were used per sample. Each sort was conducted in triplicate using different PD patient samples. FIG. 8A shows the dot plot and gating for the nestin analysis. FIG. 8B demonstrates the results of the nestin-labeled and control cell sorts. There was nearly complete labeling of the cell samples with the nestin antibody. Neither the no-primary control (Con1) nor unstained (Con2) cell populations fell within the gate parameters. These results are consistent with a substantial homogenous population of nestin-expressing cells isolated and expanded from the human PD patient brain specimens.

Example 6—Olig1

Figure 9:
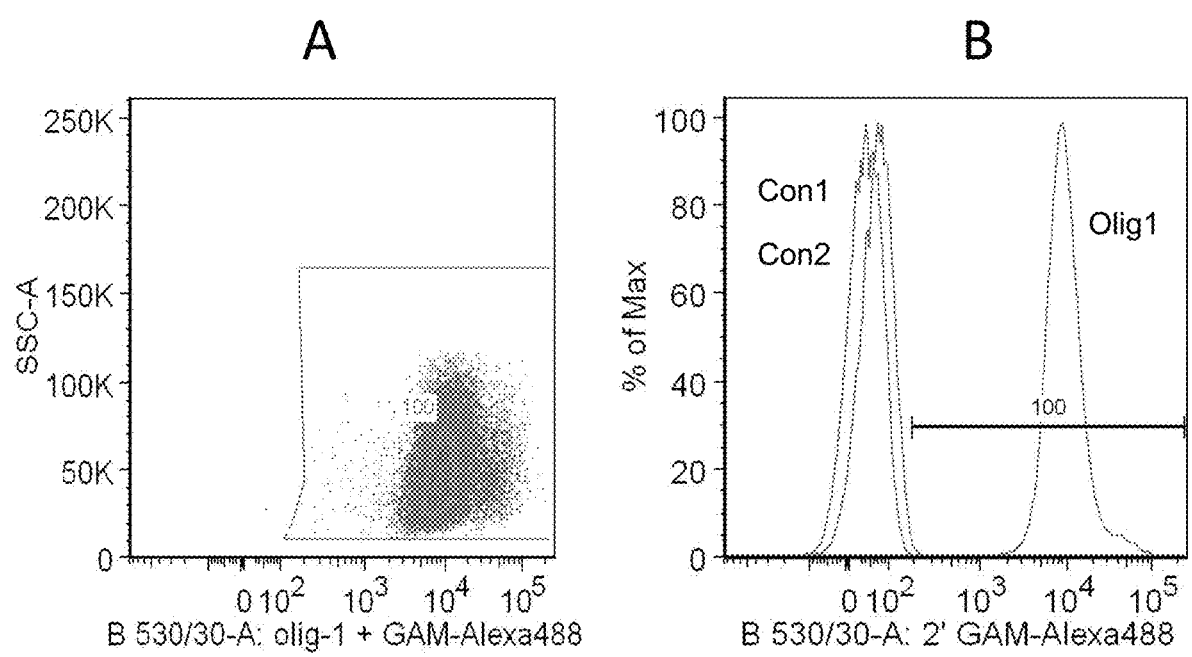
FIG. 9. Fluorescence assisted cell sorting (FACS) for Olig1-expressing cells in human PD brain cultures. A: dot plot and gating for the Olig1 analysis. B: graph illustrating the results of the Olig1-labeled and control cell sorts.

Fluorescence assisted cell sorting (FACS) for Olig1-expressing cells in human PD brain cultures. The data were acquired using a LSRII flow cytometer with FACSDiva software (BD). FACS data were analyzed with FlowJo (v9.5.2). Approximately 50,000 cells at passage 6 or 7 were used per sample. Each sort was conducted in triplicate using different PD patient samples. FIG. 9A shows the dot plot and gating for the Olig1 analysis. FIG. 9B demonstrates the results of the Olig1-labeled and control cell sorts. There was complete labeling of the cell samples with the Olig1 antibody. Neither the no-primary control (Con1) nor unstained (Con2) cell populations fell within the gate parameters. These results are consistent with a substantial homogenous population of Olig1-expressing cells isolated and expanded from the human PD patient brain specimens.

Example 7—In Vivo MRI Cell Tracking

Superparamagnetic Iron Oxide (SPIO) Labeling of Brain-Derived PD Patient Cells

A variety of iron oxide-based labels are available for preclinical research including standard SPIO particles (50-120 nm), ultra-small iron oxide agents (USPIO, 10-50 nm)

and micron-sized iron oxide particles (MPIO, 0.75 µm and larger). In this study the iron nanoparticle Molday Ion Rhodamine B (MIRB) for PD brain-derived cell tracking was used.

For the SPIO labeling of brain-derived PD patient cells, PD patient brain-derived cells are incubated for 24 h with the iron nanoparticle Molday Ion Rhodamine B (MIRB; BioPal, Worcester, MA, USA). This particle has a colloidal size of 35 nm, a zeta potential of +31 mV and is cross-linked and labeled with rhodamine B allowing visualization by both MRI and fluorescence microscopy. The cells are seeded at $8 \times 10^4$ cells/mL and incubated with an iron concentration of 50 mg/mL MIRB for 24 h. Cells are harvested and washed three times using Hanks balanced saline solution. Finally, the cells are re-suspended in Dulbecco's phosphate-buffered saline (DPBS) (Invitrogen, Grand Island, NY USA) and enumerated using an automated cell counter (The Countess, Invitrogen). To quantify the amount of intracellular iron, inductively coupled plasma-mass spectroscopy (ICP-MS, Varian 800 MS Agilent Technologies, Santa Clara, CA, USA) is performed as described previously. Perls' Prussian blue (PPB) staining is used to visualize iron oxide particles within cells. For this, the cells are fixed by methanol-acetic acid solution and stained using 2% potassium ferrocyanide in hydrogen chloride. Slides are rinsed, counterstained with eosin and passed through an alcohol dehydration series ending with xylene. Labeled cells are also examined by fluorescence microscopy using a rhodamine-specific filter.

tdTomato and MagA Transduction in Brain-Derived PD Patient Cells pLVX-IRES-(Clontech) is a lentiviral expression vector that permits simultaneous expression of a protein of interest and tdTomato in mammalian cells. PD cells are transduced with either the unaltered vector to express solely tdTomato, or following insertion of the MagA gene, resulting in co-expression of tdTomato and MagA. The MagA cDNA was obtained by polymerase chain reaction (PCR) of M. magneticum sp. AMB-1, using primers 5'-gctgccttcgtga-taagaacgcgtcc-3' (SEQ ID NO:9) and 5'-ttgagatcggcgg-catcgtca-3' (SEQ ID NO:10).

Iron-rich cultures are obtained by incubating cells for 7 days in media supplemented with 250 µM ferric nitrate (Sigma-Aldrich Canada, Oakville, ON). The cell culture conditions are intended to mimic the natural capillary bed blood supply that nourishes all cells and tissues in the body. tdTomato expression is confirmed with fluorescence microscopy and MagA expression using PCR (44). MagA-derived iron contrast is verified by ICP-MS (Analytical Service Laboratory, University of Western Ontario) and transverse relaxation rate mapping (45). In vivo imaging is performed at 3T, adapting published protocols (46).

Mouse Xenograft Model

PD cell suspension obtained as in Example 1 for implantation contains about $1 \times 10^5$ cells in 3 µl phosphate buffered saline (PBS). Adult severe combined immunodeficiency (SCID) mice (Charles River Laboratories International, Inc) receive isoflurane anesthesia and 0.05 mg/kg buprenorphine (i.p.) prior to placement in a stereotactic frame. Under aseptic conditions and through a midline scalp incision, a burrhole is made in the skull and the dura opened sharply for injections into the striatum (coordinates from bregma: anteroposterior 0 mm, lateral +/−2 mm, dorsoventral 2.5 mm). The cell suspension is infused over 5 minutes using a Hamilton syringe and micro-infusion pump and is left in place for another 4 minutes to avoid backflow of the cell suspension, after which it is removed. Analgesics will be administered twice a day for the first 3 days and sutures removed 10 days after surgery. Mouse brains and cell transplants are monitored using a 3T MRI system with a custom-built insertable gradient coil. In order to monitor cell viability and migration, volumetric striatal imaging and cell tracking is conducted on the day following cell transplant and on the final day of survival.

Immunohistochemistry and Confocal Microscopy

Animals are Euthanized at the End of the Treatment Period or Earlier if there are signs of severe neurological compromise (e.g., unable to independently eat or drink). Mice are injected with 150 mg/kg of pentobarbital sodium (i.p.). Once the animals are deeply anesthetized they are transcardially perfused with 5 ml of 0.9% saline followed by 30 ml of 4% paraformaldehyde. Brains are removed, then frozen and sectioned on a cryotome. Basic histology (i.e., Nissl stain) is used for assessing tissue integrity, and serial sections are used for iron studies (Prussian blue) and immunohistochemistry, using standard methods. Sections are mounted onto slides then washed in PBS and permeabilized for 10 minutes in PBS containing 0.25% Triton X-100. Non-specific protein binding is blocked with 1% bovine serum albumin (EMD Millipore Corp., Billerica, MA, USA) prior to incubation with primary antibodies overnight at 4° C. Sections are then washed in PBS and incubated with Alexa Fluor® 488 goat anti-mouse IgG, Alexa Fluor® 488 goat anti-rabbit IgG and/or Alexa Fluor® 546 goat anti-rabbit IgG secondary antibodies (1:100) for 1 hour at room temperature (Life Technologies Inc., Burlington, ON, Canada). The choice of secondary antibodies, or combinations thereof, will depend whether the cells express tdTomato or are labeled with rhodamine B. Control sections are processed in parallel without primary antibody. The human PD cells are identified in vivo by tdTomato or rhodamine B immunofluorescence. Naïve cells are identified using a mouse monoclonal antibody specific for human cytoplasmic marker (StemCells, Inc.). The phenotype of the transplanted human PD cells are further assessed with a panel of lineage markers that was previously evaluated in cell culture (47). Sections are imaged using a Zeiss LSM-510 META laser-scanning microscope with a Zeiss 63×NA 1.4 oil immersion lens, appropriate filters and AIM software (Carl Zeiss GmbH, Jena, Germany).

Results

Figure 10:
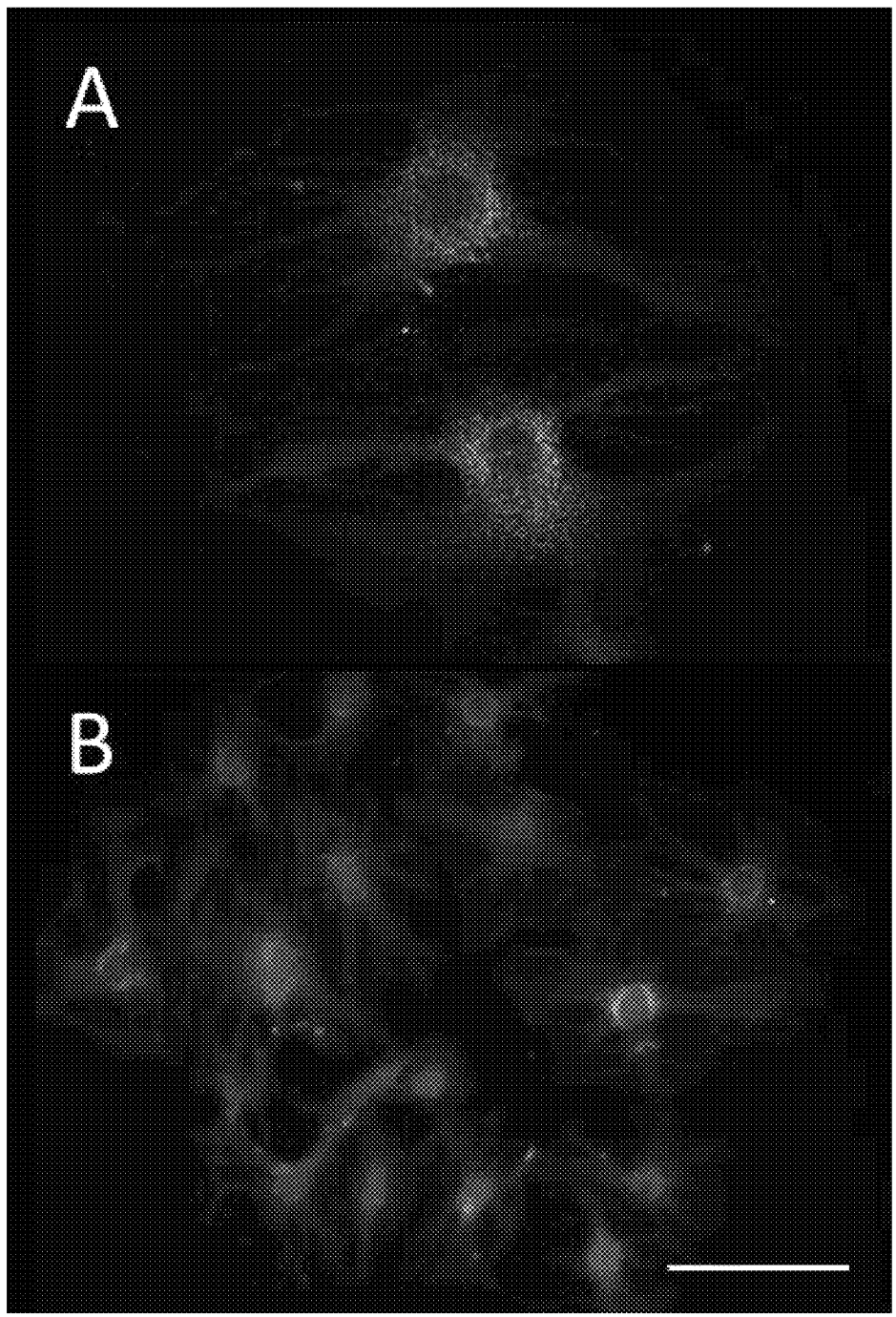
FIG. 10. Confocal fluorescence micrographs demonstrating lentivirus-transduced PD cells expressing tdTomato. (A) are examples of single cell division; (B) a clonal expansion in culture.

FIG. 10 are microphotographs showing lentivirus-transduced PD cells expressing fluorescent tdTomato single-cell division (FIG. 10A) and clonal expansion in culture (FIG. 10B). These images were taken several weeks following transduction and confirm the viability of PD brain-derived patient cells following genetic manipulation. The features of these modified cultures appear unchanged compared to naïve cells. Scale bar estimates 50 µm and 100 µm for panels A and B, respectively.

Figure 11:
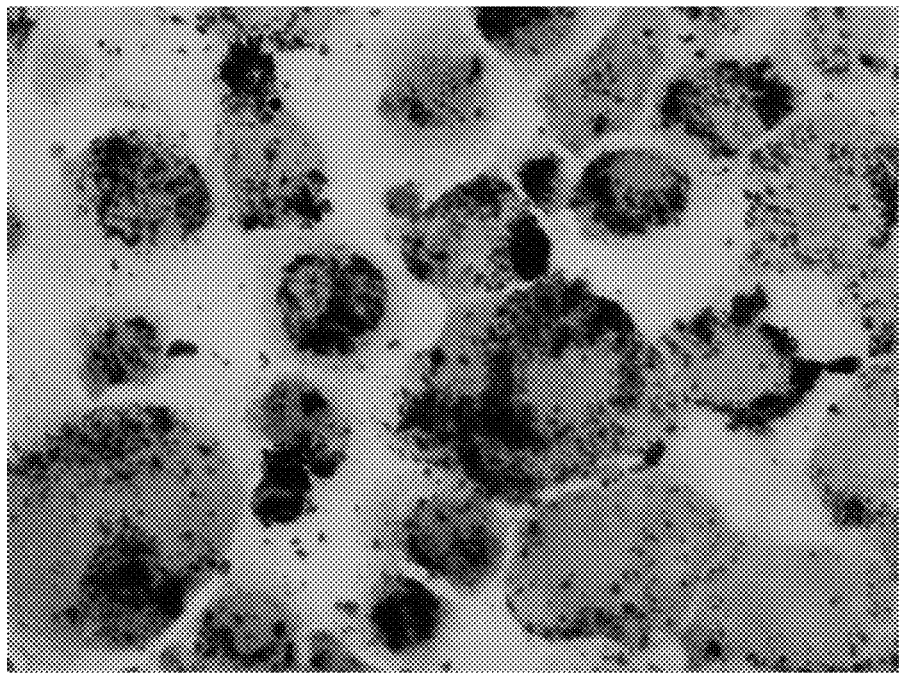
FIG. 11. Photomicrographs of human PD brain-derived cells labeled with MRI-detectable iron nanoparticles. (A) Prussian blue staining demonstrates iron particles in the human PD cells; (B) Confocal imaging of Molday-rhodamine B-labeled PD cells.
Figure 11:
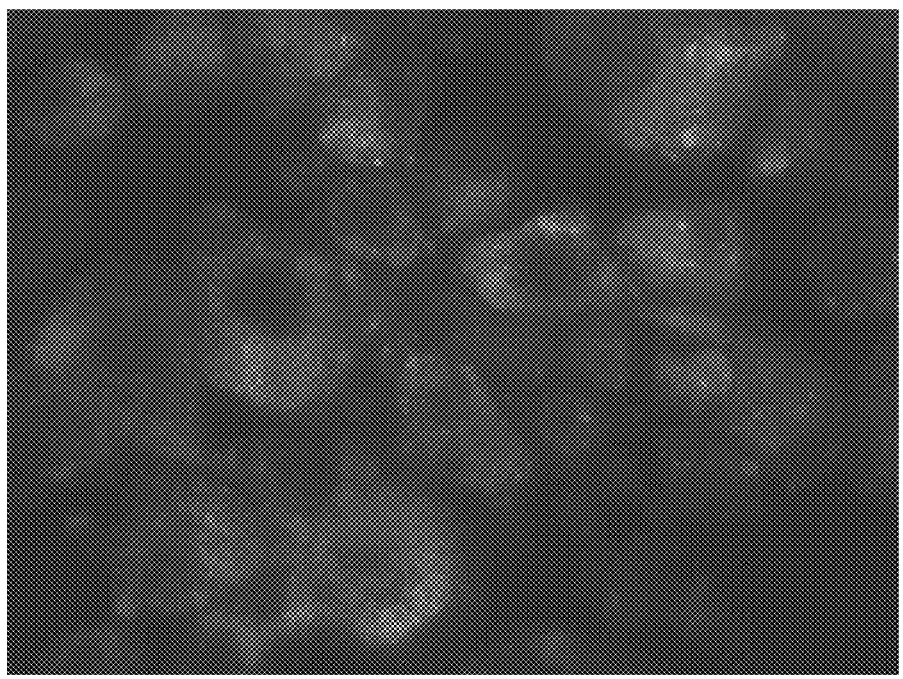

FIG. 11 shows human PD brain-derived cells labeled with MRI-detectable iron nanoparticles. FIG. 11 A is Prussian blue staining that demonstrates iron particles in the human PD cells. FIG. 11 B is a confocal imaging of Molday-rhodamine B-labeled PD cells. Molday is a 35 nm iron oxide nanoparticle with a red fluorescent tag; cells are counterlabeled with carboxyfluorescein succinimidyl ester, a green cell tracker.

Figure 12:
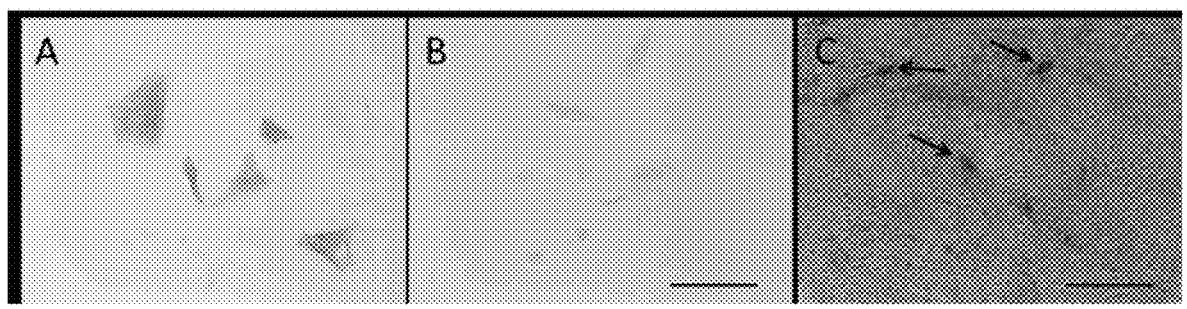
FIG. 12. Immunolabeling for human cytoplasmic antigen (STEM121 antibody, STEMCELLS Inc.) in brain-derived PD patient cells. Cells in culture showed strong labeling (A) with weak background signal in no-primary control conditions (B). Panel C shows antigen labeling using high power light microscopy through a immunodeficient mouse striatum 28 days after implantation with PD cells. Scale bar in B estimates 50 μm for panels A, B; scale bar in C estimates 100 μm.

FIG. 12 shows immunolabeling for human cytoplasmic antigen (STEM121 antibody, StemCells Inc.) in brain-derived PD patient cells. Cells in culture showed strong labeling (FIG. 12A) with weak background signal in no-primary control conditions (FIG. 12 B). Panel C of FIG. 12 shows antigen labeling using high power light microscopy through a immunodeficient mouse striatum 28 days after implantation with PD cells. The arrows indicate human cells of this study. This antibody will be used to label naïve, and co-label transduced, PD cells in vivo.

Figure 13:
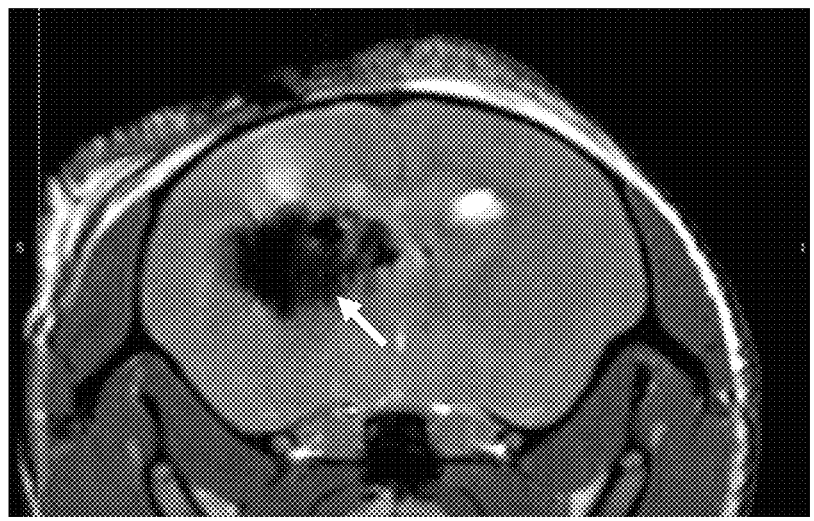
FIG. 13. Coronal MRI images of a mouse brain showing cellular MRI tracking of human PD brain-derived cells in the mouse brain. Panel A shows the cells at injection site in the striatum, panel B in the lateral ventricle, and panel C in the cerebral aqueduct.
Figure 13:
Figure 13:
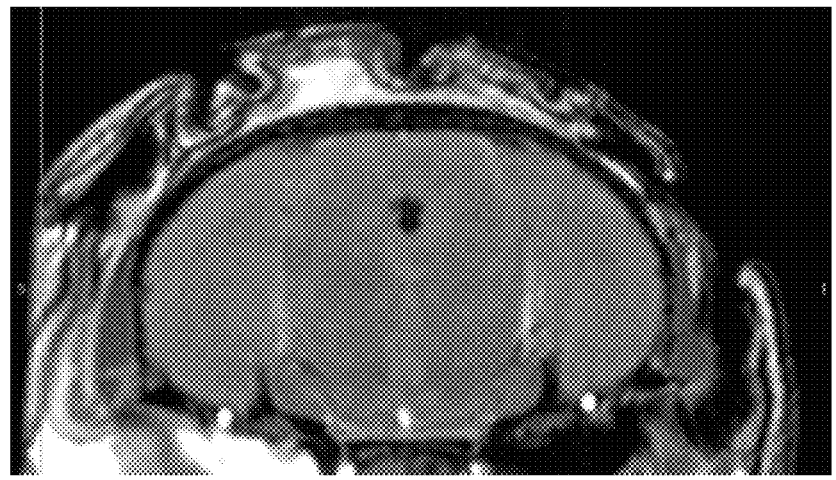

MRI photographs of PD cells labeled with Molday-rhodamine B, and imaged 2 days after transplantation into the mouse brain using a 3T MRI system are shown in FIG. 13. FIG. 13, panel A, at the site of graft deposition in the striatum, there was obvious cell signal (shown by arrow) with minimal change in surrounding brain. FIG. 13, panel B illustrates that the PD cells had encroached into the ventricular system and could be seen caudally in the temporal horn (shown by arrow). Panel C in the cerebral aqueduct. ie, the cells have dispersed through the rostrocaudal extent of the ventricular system.

Example 8—Animal Study

A reliable mouse model of Parkinson's disease (PD) may be obtained by using the neurotoxin 1-methyl-4-phenyl-1, 2,3,6-tetrahydropyridine (MPTP). A protocol for obtaining MPTP mice is provided in Jackson-Lewis V, Przedborski S., Nat Protoc. 2007; 2(1):141-51, the contents of which are entirely hereby incorporated by reference. A burr hole is made in the frontaparietal region of MPTP mice. A relatively small brain biopsy is obtained (about 0.5 µm). The brain biopsy is cultured as described in Example 1 and tested for NTF expression (neurotrophic factor (GDNF) family of ligands (GFL), neurotrophin and CDNF/MANF families). The cultured cells are also tested for at least one oligodendrogial protein (Olig1 and GalC) and at least one progenitor marker like nestin. The cultured cells are also tested for at least one mesenchymal protein such as collagen I, collagen III and fibronectin. Testing of the markers is done as described in the previous examples. The cultured cells are transplanted through the burr hole into the regions of the substantia nigra and striatum. Both autologous and non-autologous intracerebral transplantation are carried out. Controls: (a) mice receive the burr hole only (i.e. no biopsy is obtained), (b) mice receive the burr hole and biopsy is obtained, but no cells are transplanted. Neurological behavioral measurements are performed 5 days prior to making the burr hole and 1, 7, 14 and 28 weeks after the cell transplantation. Body locomotor activity is examined. The brains are evaluated histopathologically nestin-positive cells and for loss of the striatonigral dopamine system. In another series of experiments, the cultured cells are labeled with the cell marker, green fluorescent protein (GFP) and the survival and distribution of GFP-positive evaluated following intracerebral injections, as described above.

Example 9—Genetic Engineering

Cells cultured from brain biopsies are genetically modified to overexpress an NTF of interest and/or to express a gene, molecule or protein with PD therapeutic properties according to genetic engineering techniques known in the art. These genetically engineered cells are used as another group in the experiment described in Example 8.

Example 10—Discussion

Cell-based therapies offer potential to repopulate, preserve and promote regeneration of neural structure in the PD-affected brain; however reliable neural transplant substrates and methodology have not been defined. The present invention enables isolating expandable cell populations from small volume brain biopsies harvested during DBS surgery in PD patients. Most notably, cells expressed oligodendroglial proteins and a broad profile of NTFs with known cytoprotective attributes in the brain. The cultures could be rapidly propagated and remained viable following extended periods of cryostorage.

Common objectives of cell-based therapy for PD are to replenish dopamine sources or deliver NTFs into the brain. These approaches are likely to have distinct physiological consequences, with the former providing a poorly or non-regulated boost to the dopaminergic system and the latter supplying trophic molecules that, in theory, should support numerous if not all exposed CNS circuitry. Early neural transplantation studies used fetal mesencephalic grafts to increase dopamine production in the striatum. The results of open label and blinded clinical trials were highly variable and underscored the challenges of immune rejection, graft-induced dyskinesia, lack of standardized methodology and ethical opposition regarding the use of fetal tissue (21-26). It became apparent that renewable sources of graft substrate are needed, and that autologous tissues offer significant advantage over allografts, particularly with regard to immune compatibility and ethical barriers.

The present invention provides enablement that cells with intrinsic or environmentally-cued oligodendroglial character may be safely isolated and expanded from biopsies taken from the living adult PD brain. The cultures robustly expressed progenitor and neural markers, notably nestin, an intermediate filament protein found in pluripotent cells, Olig1, a transcription factor required for oligodendrocyte differentiation and GalC, a myelinassociated glycolipid (27-29). GLAST, p75NTR and SOX10 were also reliably identified. GLAST is a glutamate membrane transporter present throughout the CNS and highly expressed in glia (30) while p75NTR functions within neuronal death and survival pathways, differentiation and neurite outgrowth and is widely expressed in the developing nervous system, neural crest derivatives, and under select conditions in the adult brain (31, 32). SOX10 is a transcription factor integral to neural crest and peripheral nervous system development, and the terminal differentiation of oligodendrocytes. In the adult, SOX10 is predominantly found in oligodendrocytes, Schwann cells, melanocytes and neural crest stem cells (33-36). This marker profile is consistent with, and significantly expands upon, the findings of past studies that support the presence of glial progenitors in adult brain specimens (14-20). The current demonstration of NTFs in these preparations is novel and includes members of the GFL (i.e., GDNF), neurotrophin (i.e., BDNF) and CDNF/MANF (i.e., CDNF) families, each of which has extensive documentation of protective and/or regenerative benefits in preclinical PD models (10). The co-localization of NTFs with oligodendroglial proteins raises the intriguing prospect that these cells may effectively integrate back into the host brain as autologous glia and confer broad and enduring therapeutic function. There was also the unexpected finding of mesenchymal proteins (i.e., collagen I, collagen III, fibronectin) in Olig1- and GalC-positive cells. These and other extracellular matrix (ECM) components have been reported in normal and neoplastic glia and may reflect an iatrogenic (e.g., stress response) or native dedifferentiated state (37-41). The ECM proteins can profoundly influence cell growth and may serve to direct lamellopodia extension, migration and cellular interactions in the PD cultures (42-43).

There is a critical need for innovative and personalized approaches to treat PD. The present invention enables original methodology and phenotype characterization of autologous cell populations expanded from brain samples taken during DBS surgery in living PD patients. Standard cerebral biopsy techniques would be expected to yield similar results in individuals who are not suitable candidates for DBS. The robust, but limited, self-renewal lends these cells easily to in vitro expansion yet is likely unfavorable for neoplasia when grafted into the brain. The consistent and complex phenotype observed in these preparations holds promise for cellular integration and innate cytoprotective and trophic influence within the CNS microenvironment. Further advances in this technology may contribute to novel and much-needed therapeutic strategies for PD and other neurological diseases.

REFERENCES

1. Kosaka K., Yoshimura M., Ikeda K., and Budka H. (1984) Diffuse type of Lewy body disease: progressive dementia with abundant cortical Lewy bodies and senile changes of varying degree—a new disease? Clin. Neuropathol. 3, 185-192.
2. Braak H., Del Tredici K., Rüb U., de Vos R. A., Jansen Steur E. N., and Braak E. (2003) Staging of brain pathology related to sporadic Parkinson's disease. Neurobiol. Aging 24, 197-211.
3. Wolters E Ch. (2009) Non-motor extranigral signs and symptoms in Parkinson's disease. Parkinsonism Relat. Disord. 15, S6-12.
4. L'Episcopo F., Tirolo C., Testa N., Caniglia S., Morale M. C., and Marchetti B. (2010) Glia as a turning point in the therapeutic strategy of Parkinson's disease. CNS Neurol. Disord. Drug Targets 9, 349-372.
5. Airaksinen M. S. and Saarma M. (2002) The GDNF family: signalling, biological functions and therapeutic value. Nat. Rev. Neurosci. 3, 383-394.
6. Skaper S. D. (2008) The biology of neurotrophins, signalling pathways, and functional peptide mimetics of neurotrophins and their receptors. CNS Neurol. Disord. Drug Targets 7, 46-62.
7. Zuccato C., and Cattaneo E. (2009) Brain-derived neurotrophic factor in neurodegenerative diseases. Nat. Rev. Neurol. 5, 311-322.
8. Lindholm P., and Saarma M. (2010) Novel CDNF/MANF family of neurotrophic factors. Dev. Neurobiol. 70, 360-371.
9. Rangasamy S. B., Soderstrom K., Bakay R. A., and Kordower J. H. (2010) Neurotrophic factor therapy for Parkinson's disease. Prog. Brain Res. 184, 237-264.
10. Aron L., and Klein R. (2011) Repairing the parkinsonian brain with neurotrophic factors. Trends Neurosci. 34, 88-100.
11. Nagahara A. H. and Tuszynski M. H. (2011) Potential therapeutic uses of BDNF in neurological and psychiatric disorders. Nat. Rev. Drug Discov. 10, 209-219.
12. Ruozi B., Belletti D., Bondioli L., De Vita A., Forni F., Vandelli M. A., and Tosi G. (2012) Neurotrophic factors and neurodegenerative diseases: a delivery issue. Int. Rev. Neurobiol. 102, 207-247.
13. Okun M. S. (2012) Deep-brain stimulation for Parkinson's disease. N. Engl. J. Med. 367, 1529-1538.
14. Perzel'ová A., and Mares V. (1993) Appearance of GFAP-positive cells in adult human brain cultures spontaneously decelerated in growth. Glia 7, 237-244.
15. Perzel'ová A., Macikova I., Tardy M., Mraz P., Bizik I., and Steno J. (2007) Subpopulation of nestin positive glial precursor cells occur in primary adult brain cultures. Biologia (Bratisl) 62, 633-640.
16. Scolding N., Franklin R., Stevens S., Heldin C. H., Compston A., and Newcombe J. (1998) Oligodendrocyte progenitors are present in the normal adult human CNS and in the lesions of multiple sclerosis. Brain 121, 2221-2228.
17. Roy N. S., Wang S., Harrison-Restelli C., Benraiss A., Fraser R. A., Gravel M., Braun P. E., and Goldman S. A. (1999) Identification, isolation, and promoter-defined separation of mitotic oligodendrocyte progenitor cells from the adult human subcortical white matter. J. Neurosci. 19, 9986-9995.
18. Arsenijevic Y., Villemure J. G., Brunet J. F., Bloch J. J., Déglon N., Kostic C., Zurn A., and Aebischer P. (2001) Isolation of multipotent neural precursors residing in the cortex of the adult human brain. Exp. Neurol. 170, 48-62.
19. Brunet J. F., Pellerin L., Arsenijevic Y., Magistretti P., and Villemure J. G. (2002) A novel method for in vitro production of human glial-like cells from neurosurgical resection tissue. Lab Invest. 82, 809-812.
20. Nunes M. C., Roy N. S., Keyoung H. M., Goodman R. R., McKhann G, Jiang L., Kang J., Nedergaard M., and Goldman S. A. (2003) Identification and isolation of multipotential neural progenitor cells from the subcortical white matter of the adult human brain. Nat. Med. 9, 439-447.
21. Widner H., Tetrud J., Rehncrona S., Snow B., Brundin P., Gustavii B., Björklund A., Lindvall O., and Langston J. W. (1992) Bilateral fetal mesencephalic grafting in two patients with parkinsonism induced by 1-methyl-4-phenyl-1,2,3,6-tetrahydropyridine (MPTP). N. Engl. J. Med. 327, 1556-1563.
22. Defer G. L., Geny C., Ricolfi F., Fenelon G., Monfort J. C., Remy P., Villafane G., Jeny R., Samson Y., Keravel Y., Gaston A., Degos J. D., Peschanski M., Cesaro P., and Nguyen J. P. (1996) Long-term outcome of unilaterally transplanted parkinsonian patients. I. Clinical approach. Brain 119, 41-50.
23. Mendez I., Dagher A., Hong M., Gaudet P., Weerasinghe S., McAlister V., King D., Desrosiers J., Darvesh S., Acorn T., and Robertson H. (2002) Simultaneous intrastriatal and intranigral fetal dopaminergic grafts in patients with Parkinson disease: a pilot study. Report of three cases. J. Neurosurg. 96, 589-596.
24. Olanow C. W., Goetz C. G., Kordower J. H., Stoessl A. J., Sossi V., Brin M. F., Shannon K. M., Nauert G. M., Perl D. P., Godbold J., and Freeman T B. (2003) A double-blind controlled trial of bilateral fetal nigral transplantation in Parkinson's disease. Ann. Neurol. 54, 403-414.
25. Ma Y., Tang C., Chaly T., Greene P., Breeze R., Fahn S., Freed C., Dhawan V., and Eidelberg D. (2010) Dopamine cell implantation in Parkinson's disease: long-term clinical and (18)F-FDOPA PET outcomes. J. Nucl. Med. 51, 7-15.
26. Barker R. A., Barrett J., Mason S. L., and Björklund A. (2013) Fetal dopaminergic transplantation trials and the future of neural grafting in Parkinson's disease. Lancet Neurol. 12, 84-91.
27. Raff M. C., Mirsky R., Fields K. L., Lisak R. P., Dorfman S. H., Silberberg D. H., Gregson N. A., Leibowitz S., and Kennedy M. C. (1978) Galactocerebroside is a specific cell-surface antigenic marker for oligodendrocytes in culture. Nature 274, 813-816.
28. Baumann N., and Pham-Dinh D. (2001) Biology of oligodendrocyte and myelin in the mammalian central nervous system. Physiol. Rev. 81, 871-927.

29. Ligon K. L., Fancy S. P., Franklin R. J., and Rowitch D. H. (2006) Olig gene function in CNS development and disease. Glia 54, 1-10.
30. Maragakis N.J., and Rothstein J. D. (2001) Glutamate transporters in neurologic disease. Arch. Neurol. 58, 365-370.
31. Underwood C. K., and Coulson E. J. (2008) The p75 neurotrophin receptor. Int. J. Biochem. Cell Biol. 40, 1664-1668.
32. Ibáñez C. F., and Simi A. (2012) p75 neurotrophin receptor signaling in nervous system injury and degeneration: paradox and opportunity. Trends Neurosci. 35, 431-440.
33. Kuhlbrodt K., Herbarth B., Sock E., Hermans-Borgmeyer I., and Wegner M. (1998) Sox10, a novel transcriptional modulator in glial cells. J. Neurosci. 18, 237-250.
34. Stolt C. C., Rehberg S., Ader M., Lommes P., Riethmacher D., Schachner M., Bartsch U., and Wegner M. (2002) Terminal differentiation of myelin-forming oligodendrocytes depends on the transcription factor Sox10. Genes Dev. 16, 165-170.
35. Li H., Lu Y., Smith H. K., and Richardson W. D. (2007) Olig1 and Sox10 interact synergistically to drive myelin basic protein transcription in oligodendrocytes. J. Neurosci. 27, 14375-14382.
36. Othman A., Frim D. M., Polak P., Vujicic S., Arnason B. G. and Boullerne A. I. (2011) Olig1 is expressed in human oligodendrocytes during maturation and regeneration. Glia 59, 914-926.
37. Norton W. T., Farooq M., Chiu F. C., and Bottenstein J. E. (1988) Pure astrocyte cultures derived from cells isolated from mature brain. Glia 1, 403-414.
38. Mapstone T. B., and Galloway P. G. (1991) Expression of glial fibrillary acidic protein, vimentin, fibronectin, and N-myc oncoprotein in primary human brain tumor cell explants. Pediatr. Neurosurg. 17, 169-174.
39. Ren L. Q., Garrett D. K., Syapin M., and Syapin P. J. (2000) Differential fibronectin expression in activated C6 glial cells treated with ethanol. Mol. Pharmacol. 58, 1303-1309
40. Tom V. J., Doller C. M., Malouf A. T., and Silver J. (2004) Astrocyte-associated fibronectin is critical for axonal regeneration in adult white matter. J. Neurosci. 24, 9282-9290.
41. Gris P., Tighe A., Levin D., Sharma R., and Brown A. (2007) Transcriptional regulation of scar gene expression in primary astrocytes. Glia 55, 1145-1155.
42. Hubmacher D., and Apte S. S. (2013) The biology of the extracellular matrix: novel insights. Curr. Opin. Rheumatol. 25, 65-70.
43. Frischknecht R., and Gundelfinger E. D. (2012) The brain's extracellular matrix and its role in synaptic plasticity. Adv. Exp. Med. Biol. 970, 153-171.
44. Goldhawk D E1, Lemaire C, McCreary C R, McGirr R, Dhanvantari S, Thompson R T, Figueredo R, Koropatnick J, Foster P, Prato F S. Magnetic resonance imaging of cells overexpressing MagA, an endogenous contrast agent for live cell imaging. Mol Imaging. 2009 May-June; 8(3):129-39.
45. Sengupta A, Quiaoit K1, Thompson R T2, Prato F S2, Gelman N2, Goldhawk D E Biophysical features of MagA expression in mammalian cells: implications for MRI contrast. Front Microbiol. 2014 Feb. 5; 5:29.
46. Rohani, R., Figueredo, R., Bureau, Y., Koropatnick, J., Foster, P., Thompson, R., Prato, F., and Goldhawk, D. (2014) Imaging tumor growth non-invasively using expression of MagA or modified ferritin subunits to augment intracellular contrast for repetitive MRI, Mol Imaging Biol 16, 63-73.
47. Xu H, Belkacemi L, Jog M, Parrent A, Hebb M O Neurotrophic factor expression in expandable cell populations from brain samples in living patients with Parkinson's disease. FASEB J. 2013 October; 27(10):4157-68.

The invention claimed is:

1. A method of producing a population of expanded glial progenitor brain cells characterized as expressing nestin, an oligodendrogial protein and a mesenchymal protein and that express at least one neurotrophic factor (NTF) selected from a glial cell line-derived neurotrophic factor (GDNF), a brain-derived neurotrophic factor (BDNF), or a cerebral dopamine neurotrophic factor (CDNF), the method comprising:
    (a) culturing brain cells of a cortical and/or subcortical brain regions of a living subject under conditions suitable for cell expansion to obtain cultured cells,
    (b) testing the cultured cells for expression of nestin, the oligodendroglial protein, the mesenchymal protein and the at least one NTF, and
    (c) isolating the cultured cells that express the nestin, oligodendroglial protein, the mesenchymal protein and the at least one NTF thereby producing the population of expanded progenitor brain cells that express nestin, oligodendroglial protein, the mesenchymal protein and the at least one NTF.

2. The method of claim 1, wherein the living subject has a neurological disorder.

3. The method of claim 2, wherein the neurological disorder is selected from Parkinson's disease, Alzheimer's disease, Huntington disease and brain tissue damage caused by a cerebral ischemia.

4. The method of claim 2, wherein the method further comprises a heterologous implant of the cells isolated in step (c) in a patient having the neurological disorder.

5. The method of claim 4, wherein the neurological disorder is selected from Parkinson's disease, Alzheimer's disease, Huntington disease and brain tissue damage caused by a cerebral ischemia.

6. The method of claim 5, wherein the neurological disorder is Parkinson's disease.

7. The method of claim 2, wherein the method further comprises an autologous implant of the cells isolated in step (c) in a patient having the neurological disorder.

8. The method of claim 7, wherein the neurological disorder is selected from Parkinson's disease, Alzheimer's disease, Huntington disease and brain tissue damage caused by a cerebral ischemia.

9. The method of claim 7, wherein the neurological disorder is Parkinson's disease.

10. The method of claim 1, wherein the method further comprises genetically or physiologically manipulating the population of expanded brain cell to underexpress, express or overexpress a molecule of interest.

11. The method of claim 1, wherein step (a) comprises culturing the brain cells in a lysine coated substrate.

12. The method of claim 1, wherein prior to step (b) the method further comprises passaging the cultured cells, and wherein step (b) comprises testing the passaged cells for expression of nestin, the oligodendroglial protein, the mesenchymal protein and the at least one NTF.

13. The method of claim 12, wherein the cultured cells are passaged for a minimum of 4 passages.

14. The method of claim 1, wherein the method further comprises optimizing a culture medium by placing the population of expanded progenitor brain cells that express nestin, oligodendroglial protein, the mesenchymal protein and the at least one NTF in the culture medium.

15. The method of claim 14, wherein the method further comprises cultivating cells derived from the central nervous system in the optimized culture medium.

\* \* \* \* \*